United States Patent [19]

Myers

[11] Patent Number: 5,041,545
[45] Date of Patent: Aug. 20, 1991

[54] 2-HYDROXYBENZOPHENONE HYDRAZIDES AND DERIVATIVES THEREOF

[75] Inventor: Terry N. Myers, Williamsville, N.Y.

[73] Assignee: Atochem North America, Inc., Philadelphia, Pa.

[21] Appl. No.: 334,661

[22] Filed: Apr. 6, 1989

[51] Int. Cl.$^5$ .............. C07D 225/00; C07D 295/00; C07D 241/00; C07D 243/00

[52] U.S. Cl. .................... 540/450; 260/404; 260/404.5; 540/451; 540/454; 540/466; 540/463; 540/467; 540/470; 540/474; 540/480; 540/481; 540/482; 540/483; 540/484; 540/485; 540/487; 540/488; 540/489; 540/490; 540/492; 540/524; 540/525; 540/526; 540/527; 540/529; 540/530; 540/531; 540/544; 540/545; 540/553; 540/554; 540/596; 540/597; 540/598; 540/602; 540/603; 540/604; 540/605; 540/606; 540/607; 540/608; 540/609; 540/610; 540/611; 540/612; 544/1; 544/2; 544/3; 544/63; 544/180; 544/211; 544/212; 544/216; 544/224; 546/1; 546/14; 546/184; 546/186; 546/192; 546/207; 546/215; 546/216; 546/223; 546/225; 546/229; 546/236; 546/242; 546/244; 546/245; 546/246; 546/247; 546/248; 546/268; 546/285; 546/286; 546/304; 546/329; 548/100; 548/110; 548/146; 548/182; 548/190; 548/200; 548/206; 548/212; 548/213; 548/214; 548/215; 548/225; 548/233; 548/240; 548/243; 548/245; 548/300; 548/301; 548/356; 548/400; 548/406; 548/530; 548/541; 548/557; 548/566; 548/570; 548/577; 548/578; 549/1; 549/4; 549/9; 549/13; 549/28; 549/29; 549/59; 549/60; 549/61; 549/62; 549/63; 549/64; 549/65; 549/68; 549/69; 549/70; 549/71; 549/72; 549/73; 549/200; 549/214; 549/346; 549/356; 549/414; 549/415; 549/416; 549/424; 549/425; 549/426; 549/427; 549/428; 549/472; 549/473; 549/474; 549/475; 549/480; 556/413; 556/415; 556/416; 556/418; 556/419; 556/420; 556/421; 558/388; 558/411; 558/426; 560/8; 560/19; 560/24; 560/25; 560/27; 560/34; 564/34; 564/35; 564/36; 564/79; 564/81; 564/148; 564/149; 564/150; 564/151; 564/152

[58] Field of Search .............. 564/150, 149, 158, 157, 564/34, 35, 36, 79, 81, 148, 151, 152; 260/404, 404.5; 540/451, 454, 460, 463, 467, 470, 474, 480, 481, 482, 483, 484, 485, 487, 488, 489, 490, 492, 524, 525, 526, 527, 529, 530, 531, 544, 545, 553, 554, 596, 597, 598, 602, 603, 604, 605, 606, 607, 608, 609, 610, 611, 612; 544/1, 2, 3, 63, 180, 211, 212, 216, 224; 546/192, 207, 215, 216, 223, 225, 229, 236, 242, 245, 246, 247, 248, 268, 285, 286, 304, 329; 548/100, 110, 146, 182, 190, 200, 206, 212, 213, 214, 215, 225, 233, 240, 243, 245, 300, 301, 356, 400, 406, 530, 541, 557, 566, 570, 577, 578; 549/1, 4, 9, 13, 28, 29, 59, 60, 61, 62, 63, 64, 65, 68, 69, 70, 71, 72, 73, 200, 214, 346, 356, 414, 415, 416, 424, 425, 426, 427, 428, 472, 473, 475, 480; 556/413, 415, 416, 418, 419, 420, 421; 558/388, 411, 426; 560/8, 19, 24, 25, 27, 34

[56] References Cited

U.S. PATENT DOCUMENTS

| | | | |
|---|---|---|---|
| 2,900,388 | 8/1959 | Tien | 546/324 |
| 3,076,028 | 1/1963 | Yates et al. | 564/150 |
| 3,076,029 | 1/1963 | Yates et al. | 564/150 |
| 3,096,237 | 7/1963 | Kühle et al. | 514/603 |
| 3,210,376 | 10/1965 | Smith | 549/320 |
| 3,466,327 | 9/1969 | Tschesche et al. | 564/149 |
| 3,536,661 | 10/1970 | Hagemeyer, Jr. et al. | 524/333 |
| 3,773,830 | 11/1973 | Dexter | 564/150 |
| 3,781,319 | 12/1973 | Wawzonek et al. | 560/338 |
| 3,886,211 | 5/1975 | Keenan | 260/404.5 |
| 4,198,334 | 4/1980 | Rasberger | 524/102 |
| 4,481,315 | 11/1984 | Rody et al. | 524/89 |
| 4,493,731 | 1/1985 | Hörlein et al. | 71/118 |
| 4,547,524 | 10/1985 | Kaneko et al. | 514/594 |
| 4,692,486 | 9/1987 | Gugumus | 524/100 |

FOREIGN PATENT DOCUMENTS

| | | |
|---|---|---|
| 48-43658 | 12/1973 | Japan . |
| WO86/03760 | 7/1986 | PCT Int'l Appl. . |
| 1329847 | 9/1973 | United Kingdom . |
| 2136796A | 9/1984 | United Kingdom . |

OTHER PUBLICATIONS

Chemical Abstracts 76: 29514a (1972).
Chemical Abstracts 76: 46840w (1972).
Chemical Abstracts 77: 89053e (1972).
Chemical Abstracts 92: 119676r (1980).
Chemical Abstracts 93: 195471e (1980).

Primary Examiner—Richard L. Raymond
Assistant Examiner—Scott C. Rand
Attorney, Agent, or Firm—Panitch Schwarze Jacobs & Nadel

[57] ABSTRACT

Hydrazide functionalized 2-hydroxybenzophenone ultraviolet light and heat stabilizers and derivatives are disclosed having the general formula:

(Abstract continued on next page.)

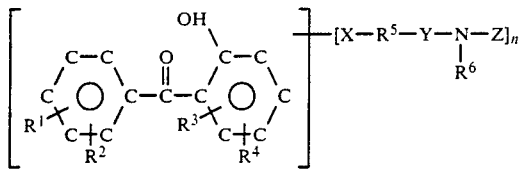

wherein $R^1$, $R^2$, $R^3$, $R^4$, $R^5$, $R^6$, X, Y, Z, all substituents thereof, and n are set forth in the Summary of the Invention. $Y-N(R^6)-Z$ is the hydrazide or derivative group and $-X-R^5-$ links the hydrazide group to an aromatic nucleus of the optionally substituted benzophenone group. Derivatives are, for example, acyl hydrazides, diacyl hydrazides (including imides), hydrazones and alkyl hydrazides. The compounds are useful as ultraviolet light absorbers and heat stabilizers for plastics.

17 Claims, No Drawings

2-HYDROXYBENZOPHENONE HYDRAZIDES AND DERIVATIVES THEREOF

CROSS-REFERENCE TO RELATED APPLICATION

This application is a continuation-in-part of copending U.S. Pat. application Ser. No. 84,599, filed Aug. 12, 1987, now abandoned.

BACKGROUND OF THE INVENTION

1. Field of the Invention

The present invention relates to certain compounds which incorporate both o-hydroxybenzophenone (ultraviolet light stabilizer) and hydrazide (heat stabilizer) functional groups.

2. Description of the Prior Art

In addition to activity as a stabilizer on a molar basis (i.e., UV absorber, antioxidant, etc.), a successful stabilizer additive must have both excellent compatibility with and/or solubility in numerous polymer substrates along with superior resistance to loss from the stabilized composition during processing and end-use application. Many stabilizer additives exhibit limited compatibility in certain substrates, and excessive tendency to exude, sublime and/or volatilize during weathering or processing of stabilized compositions, particularly when use conditions require exposure to elevated temperatures. Because of this problem, several attempts have been made to increase the compatibility and reduce the volatility of such stabilizer additives by modifying their structure. While improvements have been noted over the years, experience has shown that state-of-the-art stabilizers do not exhibit the desired combination of properties in all resins and that new polymeric compositions continue to invoke additional structural modifications on any potential heat and/or light stabilizer intended for use. Two examples of this would be in "high solids" coatings which require greater solubility of the stabilizer due to the use of less solvent, and in engineering thermoplastics where processing temperatures (in excess of 250° C.) require the use of stabilizers with high thermal stability and very low volatility. Obviously no one stabilizer to date provides the properties necessary for universal application and there is a constant commercial need for new stabilizers offering a range of property advantages.

Systems which incorporate UV absorbers and other functional groups are known. Multifunctional stabilizers have been prepared by reacting one type of stabilizer with another to obtain a higher molecular weight compound having dual functionality or by reacting two or more stabilizers with a multifunctional coupling agent (e.g. cyanuric chloride) in a stepwise fashion. U.S. Pat. No. 4,481,315 discloses molecular combinations of hydroxybenzophenones and polyalkylpiperidines. Examples of some other stabilization systems contained in one molecule can be found in U.S. Pat. Nos. 3,536,661 and 4,198,334. See Japanese Patent 73/43,658 (*Chemical Abstracts*, 81: 122589s) which discloses the use of a 2-(2-hydroxyphenyl)-2H-benzotriazole UV absorber and a hydrazide to give enhanced resistance to photodegradation of polyurethane copolymer fibers. None of this prior art discloses the present invention.

DEFINITIONS

As used herein, the term "acyl" refers to a substituent derived from a carboxylic acid group by removing the OH of the carboxyl group thereby providing a free valence, i.e., the acyl group derived from a generalized carboxylic acid D—C(=O)—OH would have the formula D—C(=O)— and would be referred to herein as a "D acyl" group.

As used herein, the terms "polymer" and "polymeric composition(s)" include homopolymers or any type of copolymers.

When any generalized functional group or index, such as $R^1$, $R^2$, a, d, etc., appears more than once in a general formula, the meaning of each is independent of one another.

SUMMARY OF THE INVENTION

This invention is directed to a compound of the formula:

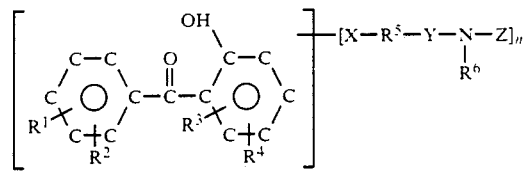

wherein $R^1$, $R^2$, $R^3$ and $R^4$ are independently hydrogen, substituted or unsubstituted aliphatic of 1–20 carbons, substituted or unsubstituted alicyclic of 5–12 carbons, substituted or unsubstituted araliphatic of 7–22 carbons, substituted or unsubstituted aliphatic acyl of 2–20 carbons, substituted or unsubstituted alicyclic acyl of 7–16 carbons, substituted or unsubstituted aryl acyl of 7–11 carbons, substituted or unsubstituted araliphatic acyl of 7–22 carbons, $—(C(=O))_a—N(R^7)(R^8)$ where a is 0 or 1, $—O—R^9$, $—S—R^{10}$, chloro, bromo, cyano, sulfamyl, or alkyl sulfamyl of 1–10 carbons.

Preferably, $R^1$, $R^2$, $R^3$ and $R^4$ are independently hydrogen, alkyl of 1–4 carbons, $—O—R^9$, aralkyl of 7–9 carbons, carboxy or chloro. Most preferably, $R^1$, $R^2$, $R^3$ and $R^4$ are independently hydrogen, $—O—R^9$ or chloro.

n is 1 or 2, and preferably n is 1.

X is $—O—$, $—N(R^{11})—$, $—S—$, $—O—C(=O)—$, $—N(R^{11})—C(=O)—$ or a direct bond between the aromatic nucleus and $R^5$. Preferably, X is $—O—$, $—O—C(=O)—$ or a direct bond between the aromatic nucleus and $R^5$. Most preferably, X is $—O—$ or a direct bond between the aromatic nucleus and $R^5$.

$R^5$ is a substituted or unsubstituted aliphatic diradical of 1–20 carbons, substituted or unsubstituted alicyclic diradical of 5–12 carbons, substituted or unsubstituted aryl diradical of 6–14 carbons or substituted or unsubstituted araliphatic diradical of 7–22 carbons; and when X is a direct bond, $R^5$ can also be a direct bond between the aromatic nucleus and Y. Preferably, $R^5$ is a substituted or unsubstituted aliphatic diradical of 1–12 carbons, substituted or unsubstituted alicyclic diradical of 5–12 carbons, substituted or unsubstituted aryl diradical of 6–12 carbons or substituted or unsubstituted araliphatic diradical of 7–12 carbons. Most preferably, $R^5$ is a substituted or unsubstituted aliphatic diradical of 1–3 carbons, substituted or unsubstituted alicyclic diradical of 5–8 carbons, substituted or unsubstituted phenylene or substituted or unsubstituted araliphatic diradical of 7–12 carbons.

Y is —C(=O)—, —S(=O)₂—, —N(R¹²)—S(=O)₂, —N(R¹²)—C(=O)— or —OC(=O)—. Preferably, Y is —C(=O)—, —S(=O)₂— or —O—C(=O)—.

R⁶ is hydrogen, substituted or unsubstituted aliphatic of 1-20 carbons, substituted or unsubstituted alicyclic of 5-12 carbons or substituted or unsubstituted araliphatic 7-22 carbons. Preferably, R⁶ is hydrogen.

R⁷, R⁸, R⁹ and R¹⁰ are independently hydrogen, substituted or unsubstituted aliphatic of 1-20 carbons, substituted or unsubstituted alicyclic of 5-12 carbons, substituted or unsubstituted aryl of 6-14 carbons or substituted or unsubstituted araliphatic of 7-22 carbons.

Preferably, R⁷, R⁸, R⁹ and R¹⁰ are independently hydrogen, substituted or unsubstituted aliphatic of 1-8 carbons, substituted or unsubstituted phenyl or substituted or unsubstituted benzyl. Most preferably, R⁷ is hydrogen, methyl or ethyl. Most preferably, R⁸ is substituted or unsubstituted aliphatic of 1-8 carbons or substituted or unsubstituted phenyl.

R¹¹ and R¹² are independently hydrogen or alkyl of 1-8 carbons. Preferably, R¹¹ and R¹² are independently hydrogen or methyl. Most preferably, R¹¹ and R¹² are hydrogen.

Z is

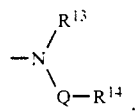

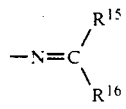

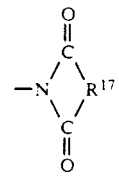

or

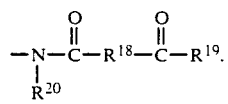

R¹³ is hydrogen, substituted or unsubstituted aliphatic of 1-20 carbons, substituted or unsubstituted alicyclic of 5-12 carbons, substituted or unsubstituted aryl of 6-14 carbons or substituted or unsubstituted araliphatic of 7-22 carbons. Preferably, R¹³ is hydrogen, substituted or unsubstituted aliphatic of 1-8 carbons, substituted or unsubstituted phenyl or substituted or unsubstituted benzyl. Most preferably, R¹³ is hydrogen, substituted or unsubstituted aliphatic of 1-8 carbons or substituted or unsubstituted phenyl.

R¹⁴ is hydrogen, substituted or unsubstituted aliphatic of 1-20 carbons, substituted or unsubstituted alicyclic of 5-12 carbons, substituted or unsubstituted aryl of 6-14 carbons, substituted or unsubstituted araliphatic of 7-22 carbons, polyoxyalkylene of general formula (I):

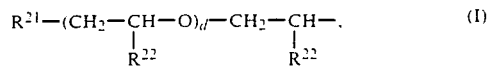

where d is an integer 2 to 50, polyalkyl of general formula CH₃—(CH₂)ₑ— where e is an integer 25 to 50, or substituted triazines of general formula

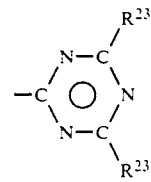

and when alicyclic, R¹⁴ optionally contains 1-6 heteroatoms —O—, —S— or —N(R²⁴)—, with the proviso that multiple heteroatoms must be separated from each other and Q by at least one carbon atom.

Preferably, R¹⁴ is hydrogen, substituted or unsubstituted aliphatic of 1-20 carbons, substituted or unsubstituted alicyclic of 5-8 carbons, substituted or unsubstituted phenyl, substituted or unsubstituted araliphatic of 7-9 carbons or polyoxyalkylene of general formula (I), and when alicyclic, R¹⁴ optionally contains 1 or 2 heteroatoms —O— or —N(R²⁴)—, with the proviso that multiple heteroatoms are separated from each other and the chain ends by at least one carbon atom. Most preferably, R¹⁴ is hydrogen, substituted or unsubstituted aliphatic of 1-10 carbons, substituted or unsubstituted cyclohexyl, substituted or unsubstituted phenyl, substituted or unsubstituted araliphatic of 7-14 carbons, polyoxyalkylene of general formula (I) and when alicyclic, R¹⁴ is substituted 2,2,6,6-tetraalkyl-4-piperidinyl.

Q is —C(=O)—, —S(=O)₂—, —C(=O)—O—, —(C(=O))₂—O—, —C(=O)—N(R²⁵)—, —(C(=O))₂—N(R²⁵)—, —C(=S)—N(R²⁵)—, —C(=O)—R¹⁸—C(=O)—N(R²⁵)— or a direct bond between the nitrogen and R¹⁴. Preferably, Q is selected from —C(=O)—, —C(=O)—O—, —(C(=O))₂—O—, —C(=O)—N(R²⁵)—, —(C(=O))₂—N(R²⁵)— or a direct bond between the nitrogen and R¹⁴. Most preferably, Q is —C(=O)—, —C(=O)—O— or a direct bond between the nitrogen and R¹⁴.

R¹⁵ and R¹⁶ are independently the same as R¹³. R¹⁵ and R¹⁶ can be linked together to form a substituted or unsubstituted alicyclic ring of 5-12 carbons or they can be linked together through a heteroatom —O—, —S— or —N(R²⁴)— to form a heterocyclic ring of 5-12 atoms. Preferably, R¹⁵ and R¹⁶ are independently substituted or unsubstituted aliphatic of 1-8 carbons, substituted or unsubstituted alicyclic of 5-8 carbons, substituted or unsubstituted aryl of 6-12 carbons, substituted or unsubstituted araliphatic of 7-14 carbons, or linked together to form a substituted or unsubstituted cycloalkyl ring of 5-8 carbons or a group of formula

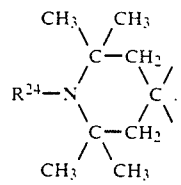

R[17] is a substituted or unsubstituted aliphatic diradical of 2-200 carbons, substituted or unsubstituted alicyclic diradical of 5-12 carbons, substituted or unsubstituted aryl diradical of 6-14 carbons or substituted or unsubstituted araliphatic diradical of 7-22 carbons. The diradical chain(s) optionally contains 1-6 heteroatoms —O—, —S— or —N(R[26])—, with the proviso that multiple heteroatoms must be separated from each other and the chain ends by at least one carbon atom. The diradical chain of R[17] must be such that the cyclic group Z formed contains 5 or 6 atoms in the ring. Preferably, R[17] is a substituted or unsubstituted aliphatic diradical of 2-20 carbons, substituted or unsubstituted alicyclic diradical of 6-8 carbons or substituted or unsubstituted aryl diradical of 6-10 carbons, and the diradical chain(s) optionally contains 1 or 2 heteroatoms —O—, —S— or —N(R[26])—, with the provisos that (a) multiple heteroatoms must be separated from each other and the chain ends by at least one carbon atom, and (b) the cyclic group Z formed contains 5 atoms in the ring.

R[18] is a substituted or unsubstituted aliphatic diradical of 1-200 carbons, substituted or unsubstituted alicyclic diradical of 5-12 carbons, substituted or unsubstituted aryl diradical of 6-14 carbons or substituted or unsubstituted araliphatic diradical of 7-22 carbons. The diradical chain(s) optionally contains 1-6 heteroatoms —O—, —S— or —N(R[26])—, with the proviso that multiple heteroatoms must be separated from each other and the chain ends by at least one carbon atom. Preferably, R[18] is a substituted or unsubstituted aliphatic diradical of 2-20 carbons, substituted or unsubstituted alicyclic diradical of 6-8 carbons or substituted or unsubstituted aryl diradical of 6-10 carbons, and the diradical chain(s) optionally contains 1 or 2 heteroatoms —O— or —N(R[26])—, with the proviso that multiple heteroatoms must be separated from each other and the chain ends by at least one carbon atom.

R[19] is R[14]—NH— or OM.

R[20] is the same as R[6]. Preferably, R[20] is selected from hydrogen, substituted or unsubstituted aliphatic of 1-8 carbons, substituted or unsubstituted alicyclic of 5-8 carbons or substituted or unsubstituted araliphatic of 7-8 carbons.

R[21] is alkoxy of 1-8 carbons, substituted or unsubstituted aryloxy of 6-10 carbons, or alkoxyalkoxy of 3 to 20 carbons.

R[22] is hydrogen or methyl.

R[23] is alkyl mercapto of 1-6 carbons, alkoxy of 1-20 carbons, or alkenyloxy of 3-7 carbons.

R[24] is hydrogen, oxyl, hydroxy, substituted or unsubstituted aliphatic of 1-20 carbons, substituted or unsubstituted alicyclic of 5-12 carbons, substituted or unsubstituted araliphatic of 7-22 carbons, substituted or unsubstituted aliphatic acyl of 2-20 carbons, substituted or unsubstituted alicyclic acyl of 7-16 carbons, substituted or unsubstituted aryl acyl of 7-11 carbons or substituted or unsubstituted araliphatic acyl of 7-22 carbons. Preferably, R[24] is hydrogen, substituted or unsubstituted aliphatic of 1-4 carbons, substituted or unsubstituted araliphatic of 7-10 carbons, substituted or unsubstituted aliphatic acyl of 2-6 carbons or substituted or unsubstituted benzoyl. Most preferably, R[24] is hydrogen, methyl, acetyl or benzoyl.

R[25] is the same group as R[13]. Preferably, R[25] is hydrogen or methyl. Most preferably R[25] is hydrogen.

R[26] is hydrogen, aliphatic of 1-8 carbons, aliphatic acyl of 2-6 carbons, or substituted or unsubstituted benzoyl. Preferably, R[26] is methyl or hydrogen.

M is hydrogen, sodium ion, potassium ion or ammonium ion. Preferably, M is hydrogen or sodium ion. Most preferably, M is hydrogen.

Optional substituents for R[1], R[2], R[3], R[4], R[5], R[6], R[7], R[8], R[9], R[10], R[11], R[12], R[13], R[14], R[15], R[16], R[17], R[18], R[20], R[21], R[22], R[24], R[25] and R[26] are independently one or more of the following: chloro, bromo, alkyl of 1-8 carbons, alkoxy of 1-12 carbons, phenoxy, cyano, hydroxy, epoxy, carboxy, benzoyl, benzoyloxy, dialkylamino of 2-8 carbons, alkyoxycarbonyl of 2-6 carbons, acyloxy of 1-4 carbons, acryloyl, acryloyloxy, methacryloyl, methacryloyloxy, hydroxymethyl, hydroxyethyl, alkylthio of 1-4 carbons or trialkoxysilyl of 3-12 carbons.

Additional optional substituents for R[13], R[15], R[16] and R[25] are independently aliphatic of 1-20 carbons, cycloaliphatic of 5-12 carbons, aryl of 6-14 carbons, aralkyl of 7-22 carbons, alkoxy of 1-20 carbons, cycloalkoxy of 5-12 carbons, aryloxy of 6-14 carbons, aralkoxy of 7-15 carbons, aliphatic acyloxy of 2-20 carbons, alicyclic acyloxy of 6-13 carbons, aromatic acyloxy of 7-15 carbons, or araliphatic acyloxy of 8-16 carbons.

Additional optional substituents for R[17] and R[18] are independently alkyl of 5-180 carbons, alkylthio of 5-180 carbons, aralkylthio of 7-20 carbons, arylthio of 6-20 carbons, alkenyl of 2-180 carbons, cycloalkenyl of 5-12 carbons, aryl of 6-16 carbons, aralkyl of 7-17 carbons, aryloxy of 6-16 carbons, alkoxycarbonyl of 7-10 carbons or (alkoxycarbonyl)alkylthio of 3-30 carbons.

DETAILED DESCRIPTION OF THE PREFERRED EMBODIMENTS

This invention is directed to a compound of the formula:

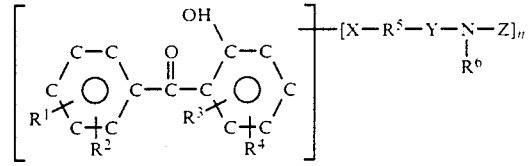

wherein R[1], R[2], R[3], R[4], R[5], R[6], X, Y, Z, all substituents thereof, and n are as previously described.

Generic Group Examples

As a substituted or unsubstituted aliphatic of 1-20 carbons, R[1], R[2], R[3], R[4], R[6], R[7], R[8], R[9], R[10], R[13], R[14], R[15], R[16], R[20], R[24] and R[25] are, for example, methyl, ethyl, n-propyl, isopropyl, butyl, allyl, hexyl, heptyl, octyl, nonyl, decyl, propargyl, octadecyl, dodecyl, isododecyl, tetradecyl, 2-methallyl, 2-hexenyl, 10-undecenyl, 2-dodecenyl, 2-hydroxyethyl, 2-butenyl, 2-hydroxyhexadecyl, 2-hydroxypropyl, 2-hydroxydodecyl, 2-hydroxy-5-hexenyl, 2-hydroxyhexyl, 2-hydroxydecyl, 2-hydroxyoctadecyl, 2-hydroxy-3-(methacryloyloxy)propyl, 2-hydroxy-3(acryloyloxy)propyl, 2-hydroxy-3-phenoxypropyl, 2-hydroxy-3-(4-methoxyphenoxy)propyl, 2-hydroxy-3isopropoxypropyl, 2-hydroxy-3-methoxypropyl, 2-hydroxy-3-(2-ethylhexyloxy)propyl, 2-hydroxy-3(cyclohexyloxy)propyl, 2-hydroxy-3-(benzyloxy)propyl, 2-hydroxy-3-(benzoyloxy)propyl, 2-hydroxy-3-dodecyloxypropyl, 2-hydroxybutyl, 1-methyl-2-hydroxypropyl, cyanomethyl, 2,3-epoxypropyl or 2-(dimethylamino)ethyl.

As a substituted or unsubstituted alicyclic of 5–12 carbons, $R^1$, $R^2$, $R^3$, $R^4$, $R^6$, $R^7$, $R^8$, $R^9$, $R^{10}$, $R^{13}$, $R^{14}$, $R^{15}$, $R^{16}$, $R^{20}$, $R^{24}$ and $R^{25}$ are, for example, cyclohexyl, trimethylcyclohexyl, cyclooctyl, cyclododecyl, 4-t-butylcyclohexyl, 2-hydroxycyclododecyl, 3-cyclohexenyl, 2-hydroxycyclohexyl, 2-hydroxycyclopentyl, 4-octylcychohexyl or 2-methyl-4-octylcyclohexyl.

As substituted or unsubstituted aryl of 6–14 carbons, $R^7$, $R^8$, $R^9$, $R^{10}$, $R^{13}$, $R^{14}$, $R^{15, R16}$ and $R^{25}$ are, for example, phenyl, tolyl, 4-chlorophenyl, isopropylphenyl, isopropenylphenyl, anisyl, 3,5-di(t-butyl)-4-hydroxyphenyl, 3,5-di(t-amyl)-4-hydroxyphenyl, 3-(t-butyl)-5-methyl-4hydroxyphenyl, naphthyl, 3-methyl-5-t-butyl-4hydroxyphenyl, 3,4,5-trimethoxyphenyl or 4-(dimethylamino)phenyl.

As a substituted or unsubstituted araliphatic group of 7–22 carbons, $R^1$, $R^2$, $R^3$, $R^4$, $R^6$, $R^7$, $R^8$, $R^9$, $R^{10}$, $R^{13}$, $R^{14}$, $R^{15}$, $R^{16}$, $R^{20}$, $R^{24}$ and $R^{25}$ are, for example, benzyl, 3-methylbenzyl, 4-t-butylbenzyl, cinnamyl, 3,5-di-t-butyl-4-hydroxybenzyl, 2-hydroxy-2-phenylethyl, 2-phenylethyl, cumyl, trimethylbenzyl, 4-octyloxybenzyl, naphthylmethyl, or (4-dodecylphenyl)methyl, 2-(3,5-di-t-butyl-4-hydroxyphenyl)ethyl, 2-(3,5-di-t-amyl-4hydroxyphenyl)ethyl or 2-(3-t-butyl-5-methyl-4-hydroxyphenyl)ethyl.

As a substituted or unsubstituted aliphatic acyl of 2–20 carbons, substituted or unsubstituted alicyclic acyl of 7–16 carbons, substituted or unsubstituted aryl acyl of 7–11 carbons or substituted or unsubstituted araliphatic acyl of 7–22 carbons, $R^1$, $R^2$, $R^3$, $R^4$, and $R^{24}$ are, for example, formyl, acetyl, chloroacetyl, acryloyl, methacryloyl, propionyl, butyryl, 2-methylpropionyl, caproyl, capryloyl, lauroyl, crotonoyl, stearoyl, octadecanoyl, cyclohexylcarbonyl, 4-t-butylcyclohexylcarbonyl, 3-cyclohexenyl-1-carbonyl, cyclododecylcarbonyl, 4-octylcyclohexylcarbonyl, 2-ethoxy-2-oxoacetyl, 2-methoxy-2-oxoacetyl, 2-methyl-4-octylcyclohexylcarbonyl, benzoyl, toluoyl, 4-chlorobenzoyl, isopropylbenzoyl, anisoyl, hydroxybenzoyl, 3,5-di-t-butyl-4-hydroxybenzoyl, naphthoyl, 3-methyl-5-t-butyl-4-hydroxybenzoyl, 3,4,5-trimethoxybenzoyl, 4-dimethylaminobenzoyl, cinnamoyl, dihydrocinnamoyl or 3-(3,5-di-t-butyl4-hydroxyphenyl)propionyl.

As $-(C(=O))_a-N(R^7)(R^8)$, the $-N(R^7)(R^8)$ radical of $R^1$, $R^2$, $R^3$ and $R^4$ can be, for example, methylamino, butylamino, octadecylamino, dodecylamino, dimethylamino, diethylamino, dibutylamino, dihexylamino, cyclohexylamino, phenylamino, benzylamino, (4-butylphenyl)amino, alpha-naphthylamino, (phenyl)(hexyl)amino, (trimethylphenyl)(amyl)amino, diphenylamino, di(4methylphenyl)amino or (4-benzylaminophenyl)(phenyl)amino.

As a substituted or unsubstituted aliphatic diradical of 1–20 carbons, substituted or unsubstituted alicyclic diradical of 5–12 carbons, substituted or unsubstituted aryl diradical of 6–14 carbons or substituted or unsubstituted araliphatic diradical of 7–22 carbons, $R^5$ is, for example, methylene, 1,2-ethanediyl, 1,2-ethenediyl, 1,3-propanediyl, 1,2-propenediyl, 1-ohloro-1,2-ethenediyl, 1-phenyl-1,2-ethenediyl, 1,3-hexanediyl, 1,2-oyclohexanediyl, 1,2-phenylene, 4-methyl-4-cyclohexene-1,2-diyl, 4-cyclohexene-1,2-diyl, 4-methylcyclohexane-1,2-diyl, norbornane-2,3-diyl, 5-norbornene-2,3-diyl, bicyclo[2.2.2]octane-2,3-diyl, bicyclo[2.2.2]-oct5-ene-2,3-diyl, bicyclo[2.2.1]heptane-1,2-diyl, bicyclo[2.2.1]heptane-1,2-diyl, 4-carboxy-1,2-phenylene, 4-methoxycarbonyl-1,2-phenylene,-3-oxapentane-1,5diyl, 1,2-phenylene, 1,3-phenylene, or 1,4-phenylene, 1,2-phenylene bismethyl, 1,3-phenylene bismethyl, 1,4-phenylene bismethyl, 2,5-diazahexane-1,6-diyl, biphenyl-4,4,-diyl, biphenyl-3,3,-diyl, biphenyl-3,4,-diyl, methylene bisphenylene, 1-(substituted)ethane-1,2-diyl wherein the substituent is selected from hydrogen, chloro, phenyl, methyl, ethyl, propyl, butyl, hexyl, octyl, decyl, dodecyl, hexadecyl, octadecyl, hexenyl, isohexenyl, diisobutenyl, decenyl, dodecenyl, isododecenyl, octenyl, nonenyl, tetradecenyl, hexadecenyl, octadecenyl or isooctadecenyl.

When alicyclic and optionally containing 1–6 heteroatoms $-O-$, $-S-$ or $-N(R^{24})-$, with the proviso that multiple heteroatoms must be separated from each other and the chain ends by at least one carbon atom, $R^{14}$ is, for example, 2,2,6,6-tetramethyl-4-piperidinyl, 2,6-diethyl-1,2,3,6-tetramethyl-4-piperidinyl, 1-acetyl-2,2,6,6-tetramethyl-4-piperidinyl or 1-(4-methylbenzoyl)2,6-dimethyl-2,6-dipropyl-3-ethyl-4-piperidinyl.

When linked together to form a substituted or unsubstituted ring of 5–12 carbons, or linked together through a heteroatom $-O-$, $-S-$ or $-N(R^{24})-$, to form a heterocyclic ring of 5–12 atoms, $R^{15}$ and $R^{16}$ are, for example, cyclopentyl, cyclohexyl, cycloheptyl, 4-t-butylcyclohexyl, 2methylcyclohexyl, cyclooctyl, 2,2,6,6-tetramethyl-4-piperidinyl, 2,6-diethyl-2,3,6-trimethyl-4-piperidinyl, 1,2,2,6,6-pentamethyl-4-piperidinyl, 1-acetyl-2,2,6,6-tetramethyl-4-piperidinyl, 1-ethyl-2,2,6,6-tetramethyl-4-piperidinyl, 4-oxacyclohexyl, or 4-thiacyclohexyl.

As a substituted or unsubstituted aliphatic diradical of 2–200 carbons, substituted or unsubstituted alicyclic diradical of 5–12 carbons, substituted or unsubstituted aryl diradical of 6–14 carbons or substituted or unsubstituted araliphatic diradical of 7–22 carbons, the diradical chain(s) of which may optionally contain 1–6 heteroatoms $-O-$, $-S-$ or $-N(R^{23})-$, with the provisos that (a) multiple heteroatoms must be separated from each other and the chain ends by at least one carbon atom and (b) that the cyclic group formed contains at least 5 atoms in the ring, $R^{17}$ is, for example, 1,2-ethanediyl, 1,2-ethenediyl, 1,3-propanediyl, 1,2propenediyl, 2-thiapropane-1,3-diyl, 3-thiapentane-1,2-diyl, 2-oxapropane-1,3-diyl, 1-chloro-1,2-ethenediyl, 1-phenyl-1,2-ethenediyl 1,3-hexanediyl, 2-azapropane-1,3-diyl, 2-methyl-2-azapropane-1,3-diyl, 1,2-cyclohexanediyl, 1,2-phenylene, 4-methyl-4-cyclohexene-1,2-diyl, 4-cyclohexene-1,2-diyl1,4-methylcyclohexane-1,2-diyl, norbornane-2,3-diyl, 5-norbornene-2,3-diyl, bicyclo[2.2.2]octane-2,3-diyl, bicyclo[2.2.2]-oct5-ene-2,3-diyl, bicyclo[2.2.1]heptane-1,2-diyl, bicyclo[2.2.1]heptane-1,2-diyl, 4-carboxy-1,2phenylene, 4-methoxycarbonyl-1,2-phenylene, propane-2,2-bis[4-cyclohexyl], 3-oxapentane-1,5diyl, methylenebis[4-cyclohexyl], 1,2-phenylene, 1,3-phenylene, 1,4-phenylene, 1,2-phenylene bismethyl, 1,3-phenylene bismethyl, 1,4-phenylene bismethyl, 2,5-diazahexane-1,6-diyl, biphenyl-4,4'-diyl, biphenyl-3,3'-diyl, biphenyl-3,4'-diyl, methylene bisphenylene, 1-(substituted)ethane-1,2-diyl wherein the substituent is selected from hydrogen, chloro, phenyl, methyl, ethyl, propyl, butyl, hexyl, octyl, decyl, dodecyl, hexadecyl, octadecyl, hexenyl, isohexenyl, diisobutenyl, decenyl, dodeceny, isododecenyl, octenyl, nonenyl, tetradecenyl, hexadecenyl, octadecenyl, isooctadecenyl, triacontenyl, and polyisobutenyl; or 1-(substituted)ethane-1,2-diyl, 5-(substituted)norbornane-2,3-diyl, 5-(substituted)bicyclo[2.2.2]octane-2,3-diyl, or 4-(substituted)cyclohexane-1,2-diyl, wherein the substituent is selected from methylthio, ethylthio, butylthio, hexylthio, octylthio, hexadecylthio, octadecylthio, 2-hydroxyethylthio, phenylthio, benzylthio, (3,5-di-t-butyl-4-hydroxy)phenylthio, or (3-t-butyl-5-methyl-4-hydroxyphenyl)benzylthio.

As a substituted or unsubstituted aliphatic diradical of 1-200 carbons, substituted or unsubstituted alicyclic diradical of 5-12 carbons, substituted or unsubstituted aryl diradical of 6-14 carbons or substituted or unsubstituted araliphatic diradical of 7-22 carbons, the diradical chain(s) of which may optionally contain 1-6 heteroatoms —O—, —S— or —N($R^{23}$)— with the provisos that multiple heteroatoms must be separated from each other and the chain ends by at least one carbon atom, $R^{18}$ is, for example methylene, 1,2-ethanediyl, 1,2-ethenediyl, 1,3-propanediyl, 1,2-propenediyl, 2-thiapropane-1,3-diyl, 3-thiapentane-1,2-diyl, 2-oxapropane-1,3-diyl, 1-chloro-1,2-ethenediyl, 1-phenyl-1,2-ethenediyl, 1,3-hexanediyl, 2-azapropane-1,3-diyl, 2-methyl-2-azapropane-1,3diyl, 1,2-cyclohexanediyl, 4-methyl-4-cyclohexene-1,2-diyl, 4-cyclohexene-1,2-diyl, 4-methylcyclohexane-1,2-diyl, norbornane-2,3-diyl, 5-norbornene-2,3-diyl, bicyclo[2.2.2]octane-2,3-diyl, bicyclo[2.2.2]oct-5-ene-2,3-diyl, bicyclo[2.2.1]heptane-1,2-diyl, bicyclo[2.2.]heptane-1,2-diyl, 4-carboxy-1,2phenylene, 4-methoxycarbonyl-1,2-phenylene, propane-2,2-bis(4-cyclohexyl), 3-oxapentane-1,5diyl, methylene bis(4-cyclohexyl), 1,2-phenylene, 1,3-phenylene, 1,4-phenylene, 1,2-phenylene bismethyl, 1,3-phenylene bismethyl, or 1,4-phenylene bismethyl, 2,5-diazahexane-1,6-diyl, biphenyl-4,4'-diyl, biphenyl-3,3'-diyl, biphenyl-3,4'-diyl, methylene bisphenylene, 1-(substituted)ethane-1,2-diyl, wherein the substituent is hydrogen, chloro, phenyl, methyl, ethyl, propyl, butyl, hexyl, octyl, decyl, dodecyl, hexadecyl, octadecyl, hexenyl, isohexenyl, diisobutenyl, decenyl, dodecenyl, isododecenyl, octenyl, nonenyl, tetradecenyl, hexadecenyl, octadecenyl, isooctadecenyl, triacontenyl or polyisobutenyl; or 1-(substituted)ethane-1,2-diyl, 5-(substituted)norbornane-2,3-diyl, 5-(substituted)bicyclo[2.2.2]octane-2,3-diyl or 4-(substituted)cyclohexane-1,2-diyl wherein the substituent is methylthio, ethylthio, butylthio, hexylthio, octylthio, hexadecylthio, octadecylthio, 2-hydroxyethylthio, phenylthio, benzylthio, (3,5-di-t-butyl-4-hydroxy)phenylthio or (3-t-butyl-5-methyl-4-hydroxyphenyl)benzylthio.

EXAMPLES OF COMPOUNDS

Examples of stabilizer compounds of this invention include the following non-limiting list:
1. 2-(4-benzoyl-3-hydroxyphenoxy)propionyl hydrazide
2. 4-(4-methylbenzoyl)-3-hydroxyphenoxyacetyl hydrazide
3. N-[4-(2,4-dimethoxybenzoyl)-3hydroxyphenoxyacetyl]-N'-[(n-octylamino)carbonyl]hydrazine
4. 4-(4-benzoyl-3-hydroxyphenoxy)-N-(tetrahydro-4-methylphthalimido)butanamide
5. 3-(4-benzoyl-3-hydroxyphenoxy)propionyl hydrazide, acetophenone hydrazone
6. N-[4-(4-ethoxybenzoyl)-3-hydroxyphenoxyacetyl]-N',N'-di(2-hydroxypropyl)hydrazine
7. N-(4-benzoyl-3-hydroxyphenoxyacetyl)-N'-(2-carboxybenzoyl)hydrazine
8. N-[4-(2,4-dichlorobenzoyl)-3hydroxyphenoxyacetyl]-N'-(6-carboxy-4thiahexanoyl)hydrazine, sodium salt
9. N-(5-benzoyl-4-hydroxy-2-methoxybenzenesulfonyl)-N'-phenylhydrazine
10. N-{4-[4-(dimethylamino)benzoyl]-3-hydroxyphenoxyacetyl}-N'-(2-phenoxyethoxycarbonyl)hydrazine
11 2-(4-benzoyl-3-hydroxyphenoxy)-N-(2-octadecenylsuccinimido)acetamide
12 4-(2,4-dimethoxybenzoyl)-3-hydroxyphenoxyacetyl hydrazide
13. 4-(4-benzoyl-3-hydroxyphenoxy)butanoyl hydrazide
14. N-[3-(4-benzoyl-3-hydroxyphenoxy)propionyl]-N'-methylhydrazine
15. N-[4-(4-ethoxybenzoyl)-3-hydroxyphenoxyacetyl]-N'-(2-hydroxypropyl)hydrazine
16. N-[4-(2,4-dichlorobenzoyl)-3-hydroxyphenoxyacetyl]-N'-(6-carboxy-4-thiahexanoyl) hydrazide
17. N-[(4-benzoyl-3-hydroxyphenoxy)acetamido]tetrabromophthalimide Utility The novel stabilizers of this invention are very effective additives for the stabilization of polymeric compositions which are normally subject to thermal and actinic light degradation. At times it may be beneficial to add other additives, discussed hereinafter, which will act as synergists with the 2-hydroxybenzophenone stabilizing group of the compounds of this invention.

The novel stabilizers of this invention can be blended with various polymeric compositions in high concentrations to form masterbatches which can then be blended with additional polymer either of the same or different type.

The amount of stabilizer used to stabilize the polymeric composition will depend on the particular polymer system to be stabilized, the degree of stabilization desired and the presence of other stabilizers in the composition. Normally it is advisable to have about 0.01% to about 5% by weight of the 2-hydroxybenzophenone moiety of the compound of this invention present in the polymeric composition. An advantageous range is from about 0.05% to about 3% by weight of the 2-hydroxybenzophenone portion of the molecule in the final composition. In some cases, about 0.5% to about 1% by weight is sufficient. Preferably, the novel stabilizer compounds are in the cyclic imide form in the final state of the stabilized polymeric composition.

In addition, the hydrazide functionalized 2-hydroxybenzophenone stabilizers (where Z is —NH$_2$) are reactive additives that can be attached to coreactive polymers to form polymer bound additives containing photooxidative and thermaloxidative stabilizing groups. Once reacted with the coreactive polymers, the stabilizer groups become chemically bound to the polymers and will not be lost via volatilization, migration or extraction.

Non-limiting examples of polymeric compositions which may be stabilized by these novel stabilizer compounds of the present invention include:
1. Polyolefins, such as high, low and linear low density polyethylenes, which may be optionally cross-linked, polypropylene, polyisobutylene, poly(methylbutene-1), polyacetylene and, in general, polyolefins derived from monomers having from two to about ten carbon atoms, and mixtures thereof.
2. Polyolefins derived from diolefins, such as polybutadiene and polyisoprene.
3. Copolymers of monoolefins or diolefins, such as ethylene-propylene, propylene-butene-1, propylene-isobutylene and ethylene-butene-1 copolymer.

4. Terpolymers of ethylene and propylene with dienes (EPDM), such as butadiene, hexadiene, dicyclopentadiene and ethylidene norbornene.

5. Copolymers of alpha-olefins with acrylic acid or methacrylic acids or their derivatives, such as ethylene-acrylic acid, ethylene-methacrylic acid and ethylene-ethyl acrylate copolymers.

6. Styrenic polymers, such as polystyrene (PS) and poly(p-methylstyrene).

7. Styrenic copolymers and terpolymers, such as styrene-butadiene (SBR), styrene-allyl alcohol and styrene-acrylonitrile (SAN), styrene-acrylonitrile-methacrylate terpolymer, styrene-butadiene-styrene block copolymers (SBS), rubber modified styrenics such as styrene-acrylonitrile copolymers modified with acrylic ester polymer (ASA), graft copolymers of styrene on rubbers such as polybutadiene (HIPS), polyisoprene or styrene-butadiene-styrene block copolymers (Stereon ™ products available from Firestone Synthetic Rubber and Latex Co.), graft copolymers of styrene-acrylonitrile on rubbers such as butadiene (ABS), polyisoprene or styrene-butadiene-styrene block copolymers, graft copolymers of styrene-methyl methacrylate on rubbers such as polybutadiene (MBS), butadiene-styrene radial block copolymers (e.g. KRO 3 ™ of Phillips Petroleum Co.), selectively hydrogenated butadiene-styrene block copolymers (e.g. Kraton G ™ from Shell Chemical Co.), and mixtures thereof.

8. Polymers and copolymers derived from halogen-containing vinyl monomers, such as poly(vinyl chloride), poly(vinyl fluoride), poly(vinylidene chloride), poly(vinylidene fluoride), poly(tetrafluoroethylene) (PTFE), vinyl chloride-vinyl acetate copolymers, vinylidene chloride-vinyl acetate copolymers and ethylenetetrafluoroethylene copolymers.

9. Halogenated rubbers, such as chlorinated and/or brominated butyl rubbers or polyolefins and fluoroelastomers.

10. Polymers and copolymers derived from alpha, beta-unsaturated acids, anhydrides, esters, amides and nitriles or combinations thereof, such as polymers or copolymers of acrylic and methacrylic acids, alkyl and/or glycidyl acrylates and methacrylates, acrylamide and methacrylamide, acrylonitrile, maleic anhydride, maleimide, the various anhydride containing polymers and copolymers described in this disclosure, copolymers of the polymers set forth in this paragraph, and various blends and mixtures thereof, as well as rubber modified versions of the polymers and copolymers set forth in this paragraph.

11. Polymers and copolymers derived from unsaturated alcohols or their acylated derivatives, such as poly(vinyl alcohol), poly(vinyl acetate), poly(vinyl stearate), poly(vinyl benzoate), poly(vinyl maleate), poly(vinyl butyral), poly(allyl phthalate), poly(allyl diethylene glycol carbonate) (ADC), ethylene-vinyl acetate copolymer and ethylene-vinyl alcohol copolymers.

12. Polymers and copolymers derived from unsaturated amines such as poly(allyl melamine).

13. Polymers and copolymers derived from epoxides, such as polyethylene oxide, polypropylene oxide and copolymers thereof, as well as polymers derived from bisglycidyl ethers.

14. Poly(phenylene oxides), poly(phenylene ethers) and modifications thereof containing grafted polystyrene or rubbers, as well as their various blends with polystyrene, rubber modified polystyrenes or nylon.

15. Polycarbonates and especially the aromatic polycarbonates, such as those derived from phosgene and bisphenols such as bisphenol-A, tetrabromobisphenol-A and tetramethylbisphenol-A.

16. Polyester derived from dicarboxylic acids and diols and/or hydroxycarboxylic acids or their corresponding lactones, such as polyalkylene phthalates (e.g., polyethylene terephthalate (PET), polybutylene terephthalate (PBT), and poly(1,4dimethylcyclohexane terephthalate), or copolymers thereof) and polylactones, such as polycaprolactone.

17. Polyarylates derived from bisphenols (e.g., bisphenol-A) and various aromatic acids, such as isophthalic and terephthalic acids or mixtures thereof.

18. Aromatic copolyestercarbonates having carbonate as well as ester linkages present in the backbone of the polymers, such as those derived from bisphenols, iso- and terephthaloyl chlorides and phosgene.

19. Polyurethanes and polyureas.

20. Polyacetals, such as polyoxymethylenes and polyoxymethylenes which contain ethylene oxide as a comonomer.

21. Polysulfones, polyethersulfones and polyimidesulfones.

22. Polyamides and copolyamides which are derived from diamines and dicarboxylic acids and/or from aminocarboxylic acids or the corresponding lactones, such as the following nylons: 6, 6/6, 6/10, 11 and 12.

23. Polyimides, polyetherimides, polyamideimides and copolyetheresters.

24. Cross-linked polymers which are derived from aldehydes on the one hand and from phenols, ureas and melamine on the other hand, such as phenol-formaldehyde, urea-formaldehyde and melamine-formaldehyde resins.

25. Alkyl resins, such as glycerolphthalic acid resins and mixtures thereof with melamine-formaldehyde resins.

26. Blends of vinyl monomers and unsaturated polyester resins which are derived from copolyesters of saturated and unsaturated dicarboxylic acids with polyhydric alcohols as well as from vinyl compounds (crosslinking agents) and also halogen-containing, flame resistant modifications thereof.

27. Natural polymers such as cellulose, natural rubber as well as the chemically modified homologous derivatives thereof, such as cellulose acetates, cellulose propionate, cellulose butyrate and the cellulose ethers such as methyl and ethyl cellulose.

In addition, the novel stabilizers of this invention may be used to stabilize various combinations or blends of the above polymers or copolymers. They are particularly useful in the stabilization of polyolefins, acrylic coatings, styrenics, rubber modified styrenics, poly(phenylene oxides) and their various blends with styrenics, rubber-modified styrenics or nylon.

The novel stabilizers of this invention can be used together with other additives to further enhance the properties of the finished polymer. Examples of other additives that can be used in conjunction with the stabilizers of this invention include antioxidants, such as alkylated monophenols, alkylated hydroquinones, hydroxylated thiodiphenyl ethers, alkylidene-bisphenols, hindered phenolic benzyl compounds, acylaminophenols, esters of 3-(3,5-di-t-butyl-4hydroxyphenyl)propionic acid, esters of 3-(5-t-butyl-4-hydroxy-3-methylphenyl)propionic acid, 3-(3,5-di-t-butyl-4-hydroxyphenyl)propionic acid amides; other UV absorbers and light stabilizers, such as 2-(2'-hydroxyphenyl)-2H-benzotriazoles, benzylidene malonate esters, esters of substituted or unsubstituted benzoic acids, diphenyl acrylates, nickel chelates, oxalic acid diamides, and hindered amine light stabilizers; other additives, such as metal deactivators, phosphites and phosphonites, peroxide decomposers, fillers and reinforcing agents, plasticizers, lubricants, corrosion and rust inhibitors, emulsifiers, mold release agents, carbon black, pigments, fluorescent brighteners, both organic and inorganic flame retardants and nondripping agents, melt flow improvers and antistatic agents. Numerous examples of suitable additives of the above type are given in Canadian Patent 1,190,038.

PREPARATIVE METHODS

The novel compounds of the present invention are prepared by reacting 2-hydroxybenzophenone-substituted carboxylic acid esters and halides, sulfonic acid esters or sulfonyl halides with a primary or secondary alkylhydrazine, hydrazine or hydrazine hydrate. Typically the ester is dissolved in a polar solvent and converted to the desired hydrazide by stirring with an equivalent amount or slight excess of hydrazine, hydrazine hydrate or a primary or secondary alkylhydrazine. The reaction may proceed at room temperature or may require heating. Preferably, the hydrazinolysis reaction is carried out in methanol or ethanol at 10°–30° C., but other solvents, such as isopropanol or ethylene glycol, are also acceptable. In most cases the resulting hydrazides can be purified by recrystallization from the lower alcohols.

Non-limiting examples of suitable hydrazines include hydrazine, hydrazine hydrate, 35–85% hydrazine hydrate, methylhydrazine, ethylhydrazine, propylhydrazine, isopropylhydrazine, n-butylhydrazine, sec-butylhydrazine, n-amylhydrazine, sec-amylhydrazine, n-hexylhydrazine, n-octylhydrazine t-butylhydrazine, phenylhydrazine, benzylhydrazine and sec-octylhydrazine.

Hydrazone derivatives of this invention are prepared by reacting the hydrazides with ketones, aldehydes or formaldehyde in inert solvents, preferably in hydrocarbon solvents under azeotropic conditions. They may also be prepared by reacting hydrazones of ketones or aldehydes with 2-hydroxybenzophenone-containing esters.

The carbamoyl and thiocarbamoyl derivatives of this invention are prepared by reacting the hydrazides with isocyanates, diisocyanates, isothiocyanates or diisothiocyanates in polar aprotic solvents, such as tetrahydrofuran or dimethylformamide.

The reactions of hydrazides with ketones, aldehydes, isocyanates, diisocyanates, isothiocyanates, and diisothiocyanates are well known in the art and can occur under a wide variety of temperatures, times, solvents and concentrations. Generally a mole ratio of about 0.9:1.0 to about 1.1:1.0 of the hydrazide to the monofunctional coreactant is employed. If the coreactant is difunctional, then a mole ratio of about 1.8:2.0 to about 1.1:1.0 of the hydrazide to the difunctional coreactant is employed. If the coreactant is a compound that can easily be removed from the product, e.g., acetone or methyl ethyl ketone, lower mole ratios may be desireable. In fact, it may be desirable to use the coreactant as the solvent.

The hydrazides also react with unsubstituted or N-substituted amic acid esters in lower alcohol solutions to form 1,2-amoyl hydrazines. The reactions are normally carried out in refluxing alcohol (e.g., methanol), but may be carried out in higher boiling aprotic solvents or without solvent by heating a mixture of the two components above their melting points. The methyl and ethyl esters of N-substituted oxamates and succinamates are the preferred coreactants.

The acyl derivatives of the hydrazides of the present invention may be prepared by reacting the esters with acid hydrazides in refluxing alcohol (e.g., methanol).

The alkoxycarbonyl, cycloalkoxycarbonyl, aryloxycarbonyl and aralkoxycarbonyl derivatives of the hyrazides of this invention may be prepared by reacting the ester (as described above) with the corresponding alkyl, cycloalkyl, aryl or aralkyl carbazates in refluxing alcohol (e.g., methanol). Alternately, these derivatives may be prepared by reacting the hydrazide with a disubstituted carbonate or substituted haloformate. When a haloformate is used, an additional base (inorganic or amine), well known to those skilled in the art may be used to react with the halogen acid formed.

The novel sulfonyl derivatives of the hydrazide may be prepared by reacting the esters with the corresponding sulfonyl hydrazide.

The novel alkyl derivatives of the hydrazide may be prepared by reacting the hydrazides with epoxides. The reactions are generally carried out neat or in a minimum amount of a high boiling solvent. Reaction generally occurs quite readily at about 140° C. to about 150° C.

The hydrazide group reacts with two equivalents of the epoxide. The ratio of the unsubstituted hydrazide to the monoalkylated and dialkylated products is dependent upon the mole ratio of epoxide to hydrazide, the temperature and if a solvent is employed, the concentration of the reactants.

Non-limiting examples of suitable ketones include acetone, methyl ethyl ketone, 2-pentanone, 2-hexanone, 3-hexanone, 2-decanone, 3-methyl-2-pentanone, 4-methyl-2-pentanone, 4-methoxy-4-methyl-2-pentanone, cyclopentanone, cyclohexanone, 2,4-dimethyl-4-heptanone, 3,5-dimethyl-4-heptanone, 2,4-dimethyl-3-pentanone, 1,3-diphenylacetone, 2-octanone, 3-octanone, dihydroisophorone, 4-t-butylcyclohexanone, methyl cyclohexyl ketone, acetophenone, 2,2,6,6-tetramethyl-4-piperidone and 2,6-diethyl-2,3,6-trimethyl-4-piperidone.

Non-limiting examples of suitable aldehydes include formaldehyde, acetaldehyde, butyraldehyde, dodecyl aldehyde, 2-ethylbutyraldehyde, heptaldehyde, isobutyraldehyde, isovaleraldehyde octyl aldehyde, propionaldehyde, benzaldehyde, 3,5-di-t-butyl-4-hydroxybenzaldehyde, 2,3-dimethyl-p-anisaldehyde, 3-hydroxybenzaldehyde, 1-naphthaldehyde, salicylaldehyde, p-tolualdehyde and 2,3,4-trimethoxybenzaldehyde.

Non-limiting examples of suitable isocyanates include allyl isocyanate, benzyl isocyanate, n-butyl isocyanate, sec-butyl isocyanate, isobutyl isocyanate, t-butyl isocyanate, cyclohexyl isocyanate, ethyl isocyanate, isopropyl isocyanate, 4-methoxyphenyl isocyanate, methyl isocyanate, octadecyl isocyanate, 1-naphthyl isocyanate, phenyl isocyanate, o-tolyl isocyanate, m-tolyl isocyanate and p-tolyl isocyanate, dimethyl-m-isopropenylbenzyl isocyanate and 2-isocyanatoethyl methacrylate.

Non-limiting examples of suitable isothiocyanates include allyl isothiocyanate, benzyl isothiocyanate, 4-bromophenyl isothiocyanate, n-butyl isothiocyanate, sec-butyl isothiocyanate, isobutyl isothiocyanate, t-butyl isothiocyanate, 3-chlorophenyl isothiocyanate, cyclohexyl isothiocyanate, ethyl isothiocyanate, methyl isothiocyanate, propyl isothiocyanate, isopropyl isothiocyanate, 1-naphthyl isothiocyanate, t-octyl isothiocyanate, phenethyl isothiocyanate, phenyl isothiocyanate, o-tolyl isothiocyanate, m-tolyl isothiocyanate and p-tolyl isothiocyanates.

Non-limiting examples of suitable amic acid esters include methyl oxamate, ethyl oxamate, propyl oxamate, isopropyl oxamate, n-butyl oxamate, phenyl oxamate, methyl succinamate, ethyl succinamate, propyl succinamate, isopropyl succinamate, n-butyl succinamate, phenyl succinamate, ethyl N-(2,2,6,6-tetramethyl-4piperidinyl)oxamate, methyl N-(2,2,6,6-tetramethyl-4-piperidinyl)oxamate, ethyl N- (2,2,6,6-tetramethyl-4-piperidinyl)succinamate, methyl N-(2,2,6,6-tetramethyl-4-piperidinyl)succinamate, ethyl N-(3,5-di-t-butyl-4-hydroxyphenyl)oxamate, methyl N-(3,5-di-t-butyl-4-hydroxyphenyl)oxamate, ethyl N-(3,5-di-t-butyl-4-hydroxyphenyl)succinamate and methyl N-(3,5-di-t-butyl-4-hydroxyphenyl)succinamate.

Non-limiting examples of suitable acid hydrazides include acetyl hydrazide, propionic hydrazide, butyric hydrazide, isobutyric hydrazide, valeric hydrazide, isovaleric hydrazide, caproic hydrazide, decanoic hydrazide, lauric hydrazide, stearic hydrazide, benzhydrazide, 3,5-di-t-butyl-4-hydroxybenzhydrazide, 3-(3,5-di-t-butyl-4-hydroxyphenyl)propionic acid hydrazide, 3-(n-hexylthio)propionic acid hydrazide, (4-benzoyl-3-hydroxyphenoxy)acetyl hydrazide and 3-(dimethylaminoethylthio)propionic acid hydrazide.

Non-limiting examples of suitable carbazates include ethyl carbazate, methyl carbazate, propyl carbazate, isopropyl carbazate, butyl carbazate, cyclohexyl carbazate, cyclopentyl carbazate, cyclododecyl carbazate, phenyl carbazate, benzyl carbazate, 4-t-butylcyclohexyl carbazate, 2-ethylhexyl carbazate, 4-methylphenyl carbazate and 3-methoxyphenyl carbazate.

Non-limiting examples of suitable diaryl carbonates include diphenyl carbonate, di-(4-methylphenyl) carbonate, di-(3-methylphenyl) carbonate, di-(3-methoxyphenyl) carbonate, di-(2,6-dimethylphenyl) carbonate and di-(2,5-di-t-butylphenyl) carbonate.

Non-limiting examples of suitable sulfonyl hydrazides include benzenesulfonyl hydrazide, 4-bromobenzenesulfonyl hydrazide, 1-butanesulfonyl hydrazide, 4-t-butylbenzenesulfonyl hydrazide, p-toluenesulfonyl hydrazide, ethanesulfonyl hydrazide, methanesulfonyl hydrazide, 4-fluorobenzenesulfonyl hydrazide, 1-hexadecanesulfonyl hydrazide, isopropanesulfonyl hydrazide and 1-naphthalenesulfonyl hydrazide.

Non-limiting examples of suitable epoxides include 1,2-epoxybutane, 2,3-epoxybutane, 1,2-epoxycyclohexane, 1,2-epoxycyclododecane, 1,2-epoxyoctane, 1,2-epoxydecane, 1,2-epoxydodecane, 1,2-epoxyoctadecane, 1,2-epoxy-3-phenoxypropane, 2,3-epoxypropyl acrylate, 2,3-epoxypropyl methacrylate, 2,3-epoxypropyl 4-methoxyphenyl ether, glycidyl isopropyl ether, glycidyl n-hexyl ether, glycidyl dodecyl ether and glycidyl octadecyl ether.

The following examples are presented to provide a more detailed explanation of the present invention and are intended as illustrations and not limitations of the invention. Unless otherwise stated herein, the temperatures are in degrees Centigrade and all parts are by weight.

EXAMPLE I

Preparation of carboxylic acid hydrazide containing 2-hydroxybenzophenones

Ethyl 4-benzoyl-3-hydroxyphenoxyacetate (30.0g, 0.1 mol) and 85% hydrazine hydrate (120 ml aq. solution, 2.0 mol hydrazine, pure basis) were stirred in 300 ml isopropyl alcohol at ambient temperature for three hours. The reaction mixture was poured into 1 L of deionized water containing acetic acid (116.0g, 1.9 mol) and cooled in an ice bath. The solid precipitate was collected on a Buchner funnel, washed with additional deionized water, then slurried with a small amount of tetrahydrofuran before a final filtration. The isolated solid was dried overnight in a vacuum oven. The 4-benzoyl-3-hydroxyphenoxyacetyl hydrazide (Ia) thus obtained weighed 19.7g (0.07 mol, 70% of theory) and had a melting range of 201-203.C. Infrared spectroscopy showed multiple ketone carbonyls around 1635 $cm^{-1}$, the hydrazide carbonyl at 1675 $cm^{-1}$ and a broad combined OH and NH absorption at 2800-3400 $cm^{-1}$. The structure was further confirmed using $^1H$ and $^{13}C$ NMR spectroscopy and by elemental analysis (theoretical: 62.93% C, 4.93% H, 9.78% N; found: 62.96% C, 4.97% H, 9.71% N).

When ethyl 2-(2,4-dihydroxybenzoyl)benzoate was substituted for ethyl 4-benzoyl-3hydroxyphenoxyacetate in this preparation, the product was 2-(2,4-dihydroxybenzoyl)benzoyl hydrazide (Ib, yield 99+%, melting range 286°-292° C.). Infrared spectral data for this compound showed multiple ketone carbonyls around 1625 $cm^{-1}$, the hydrazide carbonyl at 1650 $cm^{-1}$ and a broad combined OH and NH absorption at 2400-3700 $cm^{-1}$.

EXAMPLE II

A. Preparation of 5-benzoyl-4-hydroxy-2-methoxy-benzenesulfonyl chloride

A solution of 5-benzoyl-4-hydroxy-2-methoxybenzenesulfonic acid (Uvinul MS-40, a product of BASF Wyandotte Corporation) (20.0g, 0.065 mole) and 250 ml of warm tetrahydrofuran was cooled to room temperature. A solution of 8.0g (0.10 mole) of pyridine in 25 ml tetrahydrofuran was added accompanied by an exotherm. The resulting mixture was stirred at room temperature for 30 minutes, then poured into 200 ml pentane and stirred briefly before the sulfonic acid salt (23.5g) was collected by filtration. This salt was added slowly over 15 minutes to 29.0g (0.244 mole) of thionyl chloride at 50° C. under a nitrogen atmosphere. The resulting mixture was stirred at 55° C. for 1 hour 45 minutes. The reaction mixture was poured into 600 ml of ice water to precipitate the product. The product was isolated by filtration and transferred to a separatory funnel with 200 ml chloroform. The mixture was extracted with 125 ml of 2.5% HCl, 100 ml of 2.5% HCl and 100 ml water. The organic phase was dried with anhydrous magnesium sulfate and stripped of solvent using aspirator and high vacuum systems. The product weighed 16.5g and melted at 165°-172° C.

B. Preparation of 5-benzoyl-4-hydroxy-z-methoxy-benzenesulfonyl hydrazide

Into a 125 ml 3-neck round bottom flask were placed 2.0g (0.029 mole) of hydrazine monohydrochloride and 25 ml water. In a separate flask, the sulfonyl chloride (3.3g, 0.01 mole) prepared above was dissolved in 50 ml tetrahydrofuran. The acid chloride was added to the hydrazine solution with about a 5° C. exotherm. The reaction mixture was heated to 55° C. and then allowed to stand at room temperature for 60 hours, followed by heating at 55° C. for 72 hours. The reaction mixture was transferred to a separatory funnel with 100 ml tetrahydrofuran and 50 ml saturated aqueous sodium chloride. The organic phase was separated and the aqueous layer was washed with an additional 100 ml tetrahydrofuran. The combined organic solutions were dried with anhydrous sodium sulfate and the solvent was stripped off using aspirator and high vacuum systems. The resulting solid residue was dissolved in 200 ml methanol and treated with a solution of potassium hydroxide (0.49g, 0.0075 mole) in 7 ml methanol. The resulting methanol solution was diluted with 250 ml tetrahydrofuran and the material which precipitated was isolated by filtration. The solid was slurried with another 250 ml of tetrahydrofuran and filtered again. The solid was then recrystallized from aqueous ethanol. The product melted >280° C. Infrared spectroscopy showed multiple ketone carbonyls at 1600 and 1625 cm$^{-1}$, and the sulfonyl group at 1270 cm$^{-1}$. The structure was further confirmed using proton and carbon-13 NMR spectroscopy.

EXAMPLE III

Reaction of Ia with Various Anhydrides

The hydrazide Ia (6.4g, 0.0137 mol), tetrabromophthalic anhydride (3.9g, 0.0137 mol) and 100 ml xylene were combined in a dry 200 ml flask fitted with a Dean-Stark trap. The reaction mass was heated to reflux, azeotroping the water as it formed. This process was continued for two hours. The reaction mixture was stripped of solvent using aspirator vacuum to give 10.0g of product with a melting point >280° C. The product, (IIIa), had an assay for bromine of 41.8%. The infrared spectrum of this compound showed multiple ketone carbonyls around 1620 cm$^{-1}$, and imide and amic acid carbonyl bands around 1750 cm$^{-1}$.

The following analogs were also prepared:

From homophthalic anhydride, product IIIb was obtained in 20% yield, melting at 80°-85° C., infrared bands (carbonyl): 1620, 1710 and 1760 cm$^{-1}$.

From 3-oxaglutaric anhydride, product IIIc was obtained in 99% yield, melting at 185°-189° C., infrared carbonyl bands at 1620 and 1700 cm$^{-1}$.

From 1,8-naphthoic anhydride, product IIId was obtained in 84% yield, melting at 125°-130° C., infrared carbonyl bands at 1620 and 1710 cm$^{-1}$.

From 1,4,5,6,7,7-hexachloro-5-norbornene-2,3-dicarboxylic anhydride, the product IIIe was obtained in 88% yield, melting at >200° C.(d), infrared carbonyl bands at 1625 and 1750 cm$^{-1}$.

From phthalic anhydride, product IIIf (99+% yield based on theoretical imide, infrared carbonyl bands at 1630, 1700, 1730 cm$^{-1}$) was further imidized to a composition melting at 79°-83° C., and having infrared bands at 1625 and 1750 cm$^{-1}$, by either heating the mixture neat to 320° C. or refluxing the mixture in xylene containing acetic anhydride for 2 hours.

From octadecylsuccinic anhydride, product IIIg (98% yield, melting at 103°-115° C.), was further purified by dissolving the product in methylene chloride and washing the organic phase several times with 5% sodium bicarbonate solution. The organic layer was dried over anhydrous magnesium sulfate and stripped of solvent to afford the desired compounds in 60% purified yield, melting at 118°-125° C., and having infrared carbonyl bands at 1630, 1740 cm$^{-1}$.

From octadecenylsuccinic anhydride, product IIIh (97% yield) was dissolved in 200 ml of 50/50 methyl t-butyl ether/tetrahydrofuran and washed three times with 50 ml portions of 5% sodium bicarbonate solution. The organic layer was dried over anhydrous magnesium sulfate and stripped of solvent to afford the desired compound as a yellow solid in 81% purified yield, melting at 80°-85° C., and having infrared carbonyl bands at 1630 and 1740 cm$^{-1}$.

EXAMPLE IV

Reaction of Ia with thiodiacetic anhydride

The hydrazide Ia (3.4g, 0.012 mol), thiodiacetic anhydride (2.0g, 0.014 mol) and 100 ml xylene were combined in a dry 200 ml flask fitted with a Dean-Stark trap. The reaction mass was heated to reflux, azeotroping the water as it formed. This process was continued for two hours, followed by cooling the reaction mixture and collecting the resulting solid product in a Buchner funnel. This solid was mixed with acetic acid (45g) and sodium acetate (2.7g) and the resulting mixture was heated to 70° C. for 10 minutes. The reaction was quenched by pouring the reaction mass into water and the resulting solid precipitate was isolated by filtration. The moist product was dissolved in tetrahydrofuran and dried with anhydrous magnesium sulfate. The desiccant and solvent were removed leaving 1.6g of a white crystalline solid melting at about 60° C. The infrared spectrum of this material showed multiple ketone carbonyl bands around 1610 cm$^{-1}$ and an imide carbonyl at 1720 cm$^{-1}$.

EXAMPLE V

Preparation of N-[2-(4-benzoyl-3-hydroxyphenoxy)aoetyl]-N'-benzoylhydrazine

The hydrazide Ia (3.7g, 0.013 mol), benzoyl chloride (2.0g, 0.014 mol) and 300 ml tetrahydrofuran were combined in a dried 500 ml flask under a nitrogen atmosphere. An addition funnel was attached and charged with triethylamine (1.4g, 0.014 mol) and 25 ml tetrahydrofuran. The amine solution was added dropwise over a five minute period accompanied by an increase in reaction temperature from 20° to 23° C. The reaction mixture was then stirred at ambient temperature for 1 hour. The triethylammonium chloride was filtered off and the liquid filtrate transferred to a separatory funnel with 50 ml of methyl t-butyl ether. The organic phase was washed with 50 ml of 2.5% sodium bicarbonate followed by 50 ml of water. The organic layer was dried using anhydrous sodium sulfate and ahydrous magnesium sulfate. The solvent was stripped off using aspirator and high vacuum to give 5.1g of slightly yellow crystals with a melting range of 166°-170° C. The product was obtained in 99+% yield. The infrared spectrum of this material showed multiple ketone carbonyl bands around 1630 cm$^{-1}$ and merged hydrazide carbonyls around 1720 cm$^{-1}$.

EXAMPLE VI

Hydrazones of Ia

The hydrazide Ia (3.7g, 0.013 mol), 2-heptanone (1.6g, 0.014 mol), p-toluenesulfonic acid monohydrate (0.1g) and 100 ml toluene were combined in a dried 200 ml flask fitted with a Dean-Stark trap. The reaction mixture was heated to reflux and the water was azeotropically removed for 3 hours (the reaction mixture cleared after 2 hours). The reaction mass was transferred to a separatory funnel with 50 ml methyl t-butyl ether and 200 ml toluene. The organic mixture was washed with 50 ml of 5% sodium bicarbonate causing the formation of an insoluble interface (starting hydrazide). The aqueous layer was drained off and the organic phase and interface filtered. The organic material was returned to the separatory funnel and washed with 100 ml saturated sodium chloride. The organic material was dried with anhydrous magnesium sulfate. After removing the desiccant, the solvent was stripped off using aspirator vacuum to give 3.9g of the product as white crystals melting at 85°–92° C. The infrared spectrum of this material showed multiple ketone carbonyl bands around 1620 cm$^{-1}$ and the acyl hydrazone carbonyl at 1710 cm$^{-1}$.

When 3-methylcyclohexanone was used instead of 2-heptanone, the product obtained (VIIb) melted at about 110° C. The infrared spectrum of this compound showed multiple ketone carbonyl bands at around 1630 cm$^{-1}$ and the acyl hydrazone carbonyl at 1700 cm$^{-1}$.

When 2,4-dichlorobenzaldehyde was used instead of 2-heptanone, the product (VIIc), melted at 191°–196° C. The infrared spectrum of this compound showed multiple ketone carbonyls around 1630 cm$^{-1}$ and the acyl hydrazone carbonyl at 1710 cm$^{-1}$.

EXAMPLE VII

Hydrazone of Ia and 2,2,6,6-tetramethyl-4-piperidone

The hydrazide Ia (3.4g, 0.012 mol), 2,2,6,6-tetramethylpiperidone monohydrate (3.0g, 0.017 mol), p-toluenesulfonic acid monohydrate (0.15g) and 100 ml xylenes were combined in a dried 200 ml flask. The reaction mixture was heated to reflux and the azeotrope separated for 10 hours. The reaction mass was cooled and stripped of xylenes. The resulting solid residue was slurried with 100 ml of pentane and filtered. 2.8g of product was obtained as tan crystals melting at 193°–196° C. The infrared spectrum of this compound showed multiple ketone carbonyls around 1630 cm$^{-1}$ and the acyl hydrazone carbonyl at 1700 cm$^{-1}$.

EXAMPLE VIII

Preparation of 2-(4-benzoyl-3-hydroxy phenoxy)-N'-phenylacetyl hydrazide

Ethyl 4-benzoyl-3-hydroxyphenoxyacetate (30.0g, 0.1 mol) and phenylhydrazine (14 ml, 0.14 mol) were stirred in 100 ml toluene at 75° C. for 3.5 hours followed by heating to 100° C. for 13 hours. The reaction mixture was poured, with stirring, into 300 ml of deionized water containing acetic acid (7.6g, 0.1 mol). Methyl t-butyl ether (600 ml) and the quenched reaction mixture were poured into a separatory funnel. At this point, it was necessary to keep the solution warm to prevent precipitation of the product. The aqueous phase was removed and the organic phase was washed with two 50 ml portions of 5% acetic acid and three 50 ml portions of 5% sodium bicarbonate. The warm organic solution was dried with anhydrous magnesium sulfate. The desiccant was filtered and the solvent was stripped off using aspirator and high vacuum systems. The solid residue was recrystallized from absolute ethanol, yielding 3.8g of pink crystals. The yield of product was 76% and the melting range was 138°–140° C. The infrared spectrum of this compound showed multiple ketone carbonyl bands around 1620 cm$^{-1}$ and the hydrazide carbonyl at 1740 cm$^{-1}$. Structural integrity was further confirmed using proton and carbon-13 NMR spectroscopy.

EXAMPLE IX

Preparation of (4-benzoyl-3-hydroxyphenoxy)-N'-(methacryloyl)acetyl hydrazide The hydrazide Ia (2.9g, 0.01 mol), pyridine (0.95g, 0.012 mol) and 90 ml of tetrahydrofuran were combined in a dried 125 ml flask under a nitrogen atmosphere. An addition funnel was attached and charged with methacryloyl chloride (1.15g, 0.01 mol) and 10 ml tetrahydrofuran. The acid chloride solution was added dropwise maintaining the reaction temperature at about 10° C. The reaction mixture was then stirred at ambient temperature for 4 hours. The reaction mixture was poured into a beaker containing 700 ml of water and stirred for 15 minutes. The product which precipitated was isolated by filtration and was subsequently dissolved in 700 ml of warm chloroform for drying with anhydrous magnesium sulfate. The desiccant was removed by filtration and the solvent was stripped off using aspirator and high vacuum systems. The solid was recrystallized from toluene to give 2.4g of product. The yield was 69% of product and the melting range was 153°–155° C. The infrared spectrum of this compound showed multiple ketone carbonyls around 1620 cm$^{-1}$ and merged hydrazide carbonyl absorptions at 1650–1700 cm$^{-1}$.

EXAMPLE X

Preparation of ethyl N,-[(4-benzoyl-3-hydroxyphenoxy)acetyl]hydrazinecarboxylate The hydrazide Ia (4.0g, 0.014 mol), triethylamine (1.5g, 0.015 mol) and 175 ml tetrahydrofuran were combined in a dried 500 ml flask under a nitrogen atmosphere. An addition funnel was attached and charged with ethyl chloroformate (1.6g, 0.015 mol) and 25 ml tetrahydrofuran. The reaction mixture was warmed to 45° C. prior to the slow addition of the chloroformate. After 45 min., additional chloroformate (0.8g, 0.007 mol) in 20 ml tetrahydrofuran was added and the resulting mixture was maintained at 45° C. for 1 hour. Solid sodium chloride was added and the liquid was decanted into a separatory funnel containing 150 ml of methyl t-butyl ether. The organic solution was washed with two 50 ml portions of saturated sodium bicarbonate. The ether solution was dried over anhydrous magnesium sulfate. The desiccant was filtered and the solvents removed using aspirator and high vacuum systems. 4.3g (86%) of the product was obtained as soft crystals. The infrared spectrum of this compound showed multiple ketone carbonyl bands around 1610 cm$^{-1}$ and the acyl hydrazine carboxylate carbonyls at 1710 and 1760 cm$^{-1}$.

EXAMPLE XI

Reaction of Ia with Maleic Anhydride

Maleic anhydride (2.5g, 0.025 mol) and 150 ml toluene were combined in a dried 250 ml flask under a nitrogen atmosphere. A catalytic amount of p-toluenesulfonic acid monohydrate (2–3mg) was added. The resulting mixture was refluxed for 30 minutes. The reaction mixture was cooled to ambient temperature and hydrazide Ia (5.7g, 0.02 mol) was added. The resulting reaction mixture was stirred at room temperature for 17 hours followed by warming in a 75° C. oil bath for 1 hour. The mixture was cooled to room temperature and diluted with 150 ml of methyl t-butyl ether. The solid was filtered and mixed with 100 ml of pure methyl t-butyl ether. The mixture was warmed and stirred for about 15 minutes, followed by cooling to room temperature. The resulting solid was isolated by filtration. Residual solvent was removed using a high vacuum system. The resulting pale yellow product weighed 7.2g and melted at 144°–149°. The infrared spectrum of this product showed multiple ketone carbonyls at 1620 cm$^{-1}$ and a broad band for the remaining merged carbonyls at 1710 cm$^{-1}$. The material was shown to be >90% pure by liquid chromatography. The major impurity was starting hydrazide.

EXAMPLE XII

Preparation of N-(4-hydroxy-3,5-di-t-butylbenzoyl)-2-(4-benzoyl-3-hydroxyphenoxy)acetyl hydrazide Into a 1 liter flask equipped with a thermometer, magnetic stir bar, addition funnel and reflux condenser were placed hydrazide Ia (8.6g, 0.03 mol), 4-hydroxy-3,5-di-t-butylbenzoyl chloride (8.1g, 0.03 mol) and 700 ml tetrahydrofuran. Triethylamine (3.1g, 0.031 mol) and 10 ml tetrahydrofuran were combined and charged to the addition funnel. The amine was added to the reaction mixture over about 10 minutes at a temperature of 24°–27° C., accompanied by a mild exotherm and precipitation of triethylamine hydfochloride. The resulting mixture was stirred at 27° C. for 2 hours. The reaction mixture was heated to 40°–50°C. for 1 hour followed by cooling and filtering. An additional 1 ml of triethylamine was added to the filtered solution and the resulting mixture was allowed to stand overnight at room temperature. The solvent was stripped off using aspirator vacuum to give a yellow solid weighing 16.1g. The solid was dissolved in 30 ml of methylene chloride and washed with 50 ml of 5% aqueous HCl, aqueous sodium carbonate and sodium bicarbonate. The organic phase was dried over anhydrous sodium sulfate. The desiccant was filtered and the solvent was stripped off using aspirator vacuum and high vacuum systems. The resulting product was a yellow powder weighing 11.1g and melting at 108°–112° C. The infrared spectrum of this compound showed multiple merged carbonyl bands, the strongest at 1635 cm$^{-1}$. The phenolic OH band appeared at 3640 cm$^{-1}$.

EXAMPLE XIII

A. Preparation of diethyl 2-hydroxybenzophenone-4,4'-diyloxybisacetate

Into a 250 ml round bottom flask equipped with a reflux condenser and mechanical stirrer were placed 2,4,4'-trihydroxybenzophenone (6.9g, 0.03 mol), ethyl chloroacetate (7.4g, 0.06 mol), potassium carbonate (12.4g, 0.09 mol) and 100 ml methyl ethyl ketone. This mixture was heated to reflux for 5.5 hours. The reaction mixture was cooled to room temperature and was transferred to a separatory funnel with 300 ml water, 50 ml 10% aqueous HCl and 300 ml methyl t-butyl ether. The mixture was shaken and the phases were allowed to separate. The aqueous phase was drawn off and the organic phase was washed with three 100 ml portions of water and was dried over anhydrous magnesium sulfate. The desiccant was filtered and the solvent was stripped off using aspirator vacuum to yield 10.8g of orange crystals. This product was recrystallized from 75 ml 95% ethanol to give orange crystals which were dried under high vacuum. The yield of purified material was 6.2g (51.2% of theory) melting at 99°–103° C. The identity of this product was confirmed by NMR spectroscopy.

B. Preparation of bishydrazide

The ester from the above experiment (5.9g, 0.015 mol), 85% hydrazine hydrate (18 ml) and 75 ml isopropyl alcohol were combined in a 125 ml flask equipped with a magnetic stir bar and nitrogen atmosphere. The mixture was stirred at ambient temperature for 3.5 hours. The mixture was then poured into 1 L water and stirred while acetic acid (75.6g, 1.26 mol) was added. A very fine crystalline material separated from the solution and was isolated by filtration. The product was air dried in the filtration apparatus for 2 days. 5.3g of the product was obtained as orange crystals melting at about 232° C. The IR spectrum showed multiple ketone carbonyls at 1610 cm$^{-1}$ and hydrazide carbonyls at 1660 cm$^{-1}$. Elemental analysis: calculated: 54.54% C, 4.85% H, 14.97% N, 25.64% O; found: 52.94% C, 5.11% H, 14.46% N, 27.11% O.

EXAMPLE XIV

Preparation of 2-(4-benzoyl-3-hydroxyphenoxy)ethyl carbazate

Into a 125 ml flask equipped with a magnetic stir bar, nitrogen atmosphere and addition funnel were placed 25 ml tetrahydrofuran and 3 ml 85% hydrazine hydrate. The mixture was cooled to 10° C. using an ice bath. A solution of 2-(4-benzoyl-3-hydroxyphenoxy)ethyl chloroformate (95.4% assay, 3.4g, 0.01 mol) in 25 ml tetrahydrofuran was charged into the addition funnel and added dropwise to the hydrazine solution over a 10 minute period, while maintaining the temperature at about 10° C. After the addition was complete, the solution was allowed to warm to room temperature and was stirred for 4 hours. The reaction mixture was poured into 400 ml of water. An oil separated which slowly solidified. The solid was isolated by filtration and was dried in chloroform solution using anhydrous magnesium sulfate. The desiccant was filtered away and the solvent was stripped off using aspirator and high vacuum systems to give 3.0g of sticky yellow crystals. The crystals were slurried with 15 ml methyl t-butyl ether to give 1.3g soft yellow crystals which melted at 85°–92° C. The IR spectrum showed multiple ketone carbonyls around 1620 cm$^{-1}$ and the carbazate carbonyl at 1730 cm$^{-1}$.

EXAMPLE XV

Preparation of octylphenoxypoly(ethoxy)ethyl N'-[(4-benzoyl-3-hydroxyphenoxy)acetyl]hydrazinecarboxylate Into a 250 ml round bottom flask equipped with a reflux condenser, addition funnel, magnetic stir bar, and nitrogen atmosphere were placed hydrazide Ia (2.0g, 0.007 mol), triethylamine (0.8g, 0.008 mol) and 75 ml tetrahydrofuran. The addition funnel was charged with octylphenoxypoly(ethoxy)ethyl chloroformate (5.0g, 0.007 mol by hydrolyzable chloride content) and 25 ml tetrahydrofuran. The chloroformate was added to the reaction mixture with a slight exotherm noted. After complete addition, the mixture was refluxed for 2.5 hours. The reaction mixture was cooled and the small amount of solid in the solution was removed by filtration. The solvent was stripped off using aspirator vacuum to yield a residue consisting of a solid in a viscous liquid. This was taken up in 25 ml acetone and the insoluble solid was removed by filtration. The acetone was removed using aspirator and high vacuum systems. The IR spectrum of the residue showed 3 carbonyl absorptions at 1770, 1710 and 1600 cm$^{-1}$. The product was a viscous yellow oil weighing 5.7g (85% of theory).

EXAMPLE XVI

ACCELERATED WEATHERING TEST

A. Resin Formulation

A low molecular Weight hydroxy-functional acrylic resin, or oligomer, was prepared by free radical solution polymerization. The polymerization was conducted under nitrogen in a jacketed glass reactor equipped with a stirrer, thermometer, and reflux condenser. The monomers and initiator (listed below) were combined and metered into the reactor containing ethyl 3-ethoxypropionate solvent (150g) at 145° C. over a five hour period. After the monomer/initiator addition was complete, polymerization was continued for an additional hour to reduce residual monomers.

|  | Amount |
|---|---|
| Monomers: | |
| butyl acrylate | 180 g |
| butyl methacrylate | 120 g |
| 2-hydroxyethyl acrylate | 150 g |
| methyl methacrylate | 72 g |
| styrene | 60 g |
| methacrylic acid | 18 g |
| Initiator: | |
| Lupersol 533 M75 (ethyl-3,3-di-(t-amylperoxy)butyrate, 75% in odorless mineral spirits) | 40 g |

B. Sample preparation

A clear acrylic coating formulation comprised the acrylic resin prepared above, melamine crosslinking resin, acid catalyst and reducing solvents. Coatings were applied by brush onto untreated aluminum panels and cured at 140° C. for 20 minutes. Dry film thickness was typically 1.5-2.0 mils. The coating formulation was prepared with and without inclusion of stabilizer Ia.

|  | Amount |
|---|---|
| Coating: | |
| Resin (A above) | 20.0 g |
| Cymel 303 (melamine formaldehyde resin - American Cyanamid) | 5.0 g |
| n-Butanol | 2.7 g |
| Aromatic-100 (mixed aromatic hydrocarbons - Exxon Chemicals) | 2.7 g |
| DBE Solvent (dibasic esters - E. I. duPont) | |
| Cycat 4040 (40% wt solution of p-toluenesulfonic acid in isopropanol - American Cyanamid) | 0.2 g |
| (Stabilizer Ia) | (0.2 g) |

C. Accelerated Weathering

Cured coatings were aged at room temperature for 24 hours, after which gloss (60°), pencil hardness and solvent resistance (methyl ethyl ketone rubs) were determined. Stabilized and unstabilized coatings gave similar results in these tests. Accelerated weathering was conducted with a Q-U-V weathering instrument using an 8-hour light cycle (UV-B) at 60° C., and a 4 hour wet cycle at 50° C. Exposed panels were inspected at regular intervals for loss in gloss. This was determined by the average of three panel measurements. The test results are shown in the following table and demonstrate the effectiveness of the stabilizer Ia for retaining initial coating properties.

TABLE I

| | Accelerated Weathering Results | | | | |
|---|---|---|---|---|---|
| | % gloss retention after exposure (hrs) | | | | |
| Stabilizer | 0 | 750 | 1000 | 1200 | 1450 |
| Ia | 100 | 98 | 91 | 54 | 46 |
| None | 100 | 76 | 60 | 51 | (failed) |

The present invention may be embodied in other specific forms without departing from the spirit or essential attributes thereof and, accordingly, reference should be made to the appended claims, rather than to the foregoing specification as indicating the scope of the invention.

I claim:

1. A compound of the formula

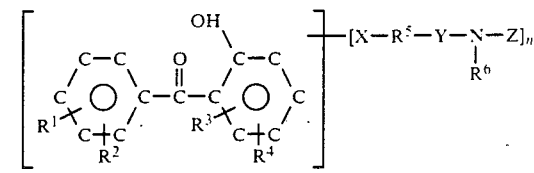

wherein
R$^1$, R$^2$, R$^3$ and R$^4$ are independently hydrogen, substituted or unsubstituted aliphatic of 1-20 carbons, substituted or unsubstituted alicyclic of 5-12 carbons, substituted or unsubstituted araliphatic of 7-22 carbons, substituted or unsubstituted aliphatic acyl of 2-20 carbons, substituted or unsubstituted alicyclic acyl of 7-16 carbons, substituted or unsubstituted aryl acyl of 7-11 carbons, substituted or unsubstituted araliphatic acyl of 7-22 carbons, —(C(=O))$_a$—N(R$^7$)(R$^8$) where a is 0 or 1, —O—$R^9$, —S—$R^{10}$, chloro, bromo, cyano, sulfamyl, or alkyl sulfamyl of 1-10 carbons;

n is 1 or 2;

X is —O—, —N($R^{11}$)—, —S—, —O—C(=O)—, —N($R^{11}$)—C(=O)— or a direct bond between the aromatic nucleus and $R^5$;

$R^5$ is a substituted or unsubstituted aliphatic diradical of 1-20 carbons, substituted or unsubstituted alicyclic diradical of 5-12 carbons, substituted or unsubstituted aryl diradical of 6-14 carbons or substituted or unsubstituted araliphatic diradical of 7-22 carbons;

when X is a direct bond, R5 is a direct bond between the aromatic nucleus and Y, a substituted or unsubstituted aliphatic diradical of 1-20 carbons, substituted or unsubstituted alicyclic diradical of 5-12 carbons, substituted or unsubstituted aryl diradical of 6-14 carbons or substituted or unsubstituted araliphatic diradical of 7-22 carbons;

Y is —C(=O)—, —S(=O)$_2$—, —N($R^{12}$)—S(=O)$_2$, —N($R^{12}$)—C(=O)— or —OC(=O)—;

$R^6$ is hydrogen, substituted or unsubstituted aliphatic of 1-20 carbons, substituted or unsubstituted alicyclic of 5-12 carbons or substituted or unsubstituted araliphatic of 7-22 carbons;

$R^7$, $R^8$, $R^9$ and $R^{10}$ are independently hydrogen, substituted or unsubstituted aliphatic of 1-20 carbons, substituted or unsubstituted alicyclic of 5-12 carbons, substituted or unsubstituted aryl of 6-14 carbons or substituted or unsubstituted araliphatic of 7-22 carbons;

$R^{11}$ and $R^{12}$ are independently hydrogen or alkyl of 1-8 carbons;

Z is

Z is

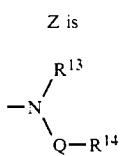

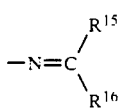

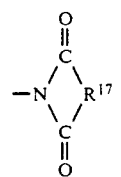

or

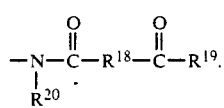

$R^{13}$ is hydrogen, substituted or unsubstituted aliphatic of 1-20 carbons, substituted or unsubstituted alicyclic of 5-12 carbons, substituted or unsubstituted aryl of 6-14 carbons or substituted or unsubstituted araliphatic of 7-22 carbons;

$R^{14}$ is hydrogen, substituted or unsubstituted aliphatic of 1-20 carbons, substituted or unsubstituted alicyclic of 5-12 carbons, substituted or unsubstituted aryl of 6-14 carbons, substituted or unsubstituted araliphatic of 7-22 carbons or polyoxyalkylene of general formula (I):

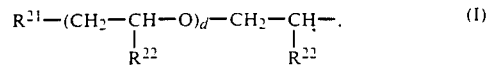

where d is an integer 2 to 50, polyalkyl of general formula $CH_3$—$(CH_2)_e$— where e is an integer 25 to 50, substituted triazines of general formula

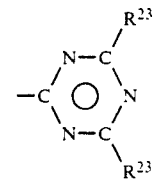

or heterocyclic of 5-12 atoms —C—, —O—, —S— or —N($R^{24}$)—, with the provisos relating to the heterocyclic group that the atom linking $R^{14}$ to Q is a carbon atom, there are no more than six non-carbon atoms, and the non-carbon atoms are separated from each other by at least one carbon atom;

Q is —C(=O)—, —S(=O)$_2$—, —C(=O)—O—, —(C(=O))$_2$—O—, —C(=O)—N($R^{25}$)—, —(C(=O))$_2$—N($R^{25}$)—, —C(=S)—N($R^{25}$)—, —C(=O)—$R^{18}$—C(=O)—N($R^{25}$)— or a direct bond between the nitrogen and $R^{14}$;

$R^{15}$ and $R^{16}$ are independently hydrogen, substituted or unsubstituted aliphatic of 1-20 carbons, substituted or unsubstituted alicyclic of 5-2 carbons, substituted or unsubstituted aryl of 6-14 carbons or substituted or unsubstituted araliphatic of 7-22 carbons, or $R^{15}$ and $R^{16}$ are linked together to form a substituted or unsubstituted alicyclic ring of 5-12 carbons or linked together through a heteroatom —O—, —S— or —N($R^{24}$— to form a heterocyclic ring of 5-12 atoms;

$R^{17}$ is a substituted or unsubstituted aliphatic diradical of 2-200 carbons, substituted or unsubstituted alicyclic diradical of 5-12 carbons, substituted or unsubstituted aryl diradical of 6-14 carbons, substituted or unsubstituted araliphatic diradical of 7-22 carbons or any of the $R^{17}$ diradicals containing 1-6 heteroatoms —O—, —S— or —N($R^{26}$)—, with the proviso that multiple heteroatoms must be separated from each other and the chain ends by at least one carbon atom, and wherein the diradical chain of $R^{17}$ must be such that the cyclic group Z formed contains 5 or 6 atoms in the ring;

$R^{18}$ is a substituted or unsubstituted aliphatic diradical of 1-200 carbons, substituted or unsubstituted alicyclic diradical of 5-12 carbons, substituted or unsubstituted aryl diradical of 6-14 carbons, substituted or unsubstituted araliphatic diradical of 7-22 carbons or any of the $R^{18}$ diradicals containing 1-6 heteroatoms —O—, —S— or —N($R^{26}$)—, with the proviso that multiple heteroatoms must be separated from each other and the chain ends by at least one carbon atom;

$R^{19}$ is $R^{14}$—NH— or OM;

$R^{20}$ is hydrogen, substituted or unsubstituted aliphatic of 1-20 carbons, substituted or unsubstituted alicyclic of 5-12 carbons or substituted or unsubstituted araliphatic of 7-22 carbons;

$R^{21}$ is alkoxy of 1-8 carbons, substituted or unsubstituted aryloxy of 6-10 carbons or alkoxyalkoxy of 3 to 20 carbons;

$R^{22}$ is hydrogen or methyl;

$R^{23}$ is alkyl mercapto of 1-6 carbons, alkoxy of 1-20 carbons or alkenyloxy of 3-7 carbons;

$R^{24}$ is hydrogen, oxyl, hydroxy, substituted or unsubstituted aliphatic of 1-20 carbons, substituted or unsubstituted alicyclic of 5-12 carbons, substituted or unsubstituted araliphatic of 7-22 carbons, substituted or unsubstituted aliphatic acyl of 2-20 carbons, substituted or unsubstituted alicyclic acyl of 7-16 carbons, substituted or unsubstituted aryl acyl of 7-11 carbons or substituted or unsubstituted araliphatic acyl of 7-22 carbons;

$R^{25}$ is hydrogen, substituted or unsubstituted aliphatic of 1-20 carbons, substituted or unsubstituted alicyclic of 5-12 carbons, substituted or unsubstituted aryl of 6-14 carbons or substituted or unsubstituted araliphatic of 7-22 carbons;

$R^{26}$ is hydrogen, aliphatic of 1-8 carbons, aliphatic acyl of 2-6 carbons or substituted or unsubstituted benzoyl; and M is hydrogen, sodium ion, potassium ion or ammonium ion;

wherein substituents for $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{20}, R^{21}, R^{24}, R^{25}$ or $R^{26}$, when substituted, are independently one or more of the following: chloro, bromo, alkyl of 1-8 carbons, alkoxy of 1-12 carbons, phenoxy, cyano, hydroxy, epoxy, carboxy, benzoyl, benzoyloxy, dialkylamino of 2-8 carbons, alkyoxycarbonyl of 2-6 carbons, acyloxy of 1-4 carbons, acryloyl, acryloyloxy, methacryloyl, methacryloyloxy, hydroxymethyl, hydroxyethyl, alkylthio of 1-4 carbons or trialkoxysilyl of 3-12 carbons;

additional substituents for $R^{13}, R^{15}, R^{16}$ or $R^{25}$, when substituted, are independently aliphatic of 1-20 carbons, cycloaliphatic of 5-12 carbons, aryl of 6-14 carbons, aralkyl of 7-22 carbons, alkoxy of 1-20 carbons, cycloalkoxy of 5-12 carbons, aryloxy of 6-14 carbons, aralkoxy of 7-15 carbons, aliphatic acyloxy of 2-20 carbons, alicyclic acyloxy of 6-13 carbons, aromatic acyloxy of 7-15 carbons or araliphatic acyloxy of 8-16 carbons; and additional substituents for $R^{17}$ or $R^{18}$, when substituted, are independently alkyl of 5-180 carbons, alkylthio of 5-180 carbons, aralkylthio of 7-20 carbons, arylthio of 6-20 carbons, alkenyl of 2-180 carbons, cycloalkenyl of 5-12 carbons, aryl of 6-16 carbons, aralkyl of 7-17 carbons, aryloxy of 6-16 carbons, alkoxycarbonyl of 7-10 carbons or (alkoxycarbonyl)alkylthio of 3-30 carbons.

2. The compound of claim 1 wherein $R^1, R^2, R^3$ and $R^4$ are independently hydrogen, alkyl of 1-4 carbons, $-O-R^9$, aralkyl of 7-9 carbons, carboxy or chloro;

n is 1;

X is $-O-$, $-O-C(=O)-$ or a direct bond between the aromatic nucleus and $R^5$;

$R^5$ is a substituted or unsubstituted aliphatic diradical of 1-12 carbons, substituted or unsubstituted alicyclic diradical of 5-12 carbons, substituted or unsubstituted aryl diradical of 6-12 carbons or substituted or unsubstituted araliphatic diradical of 7-12 carbons;

Y is $-C(=O)-$, $-S(=O)_2-$ or $-O-C(=O)-$;

$R^6$ is hydrogen;

$R^7, R^8, R^9, R^{10}$ and $R^{13}$ are independently hydrogen, substituted or unsubstituted aliphatic of 1-8 carbons, substituted or unsubstituted phenyl or substituted or unsubstituted benzyl;

$R^{11}$ and $R^{12}$ are independently hydrogen or methyl;

$R^{14}$ is hydrogen, substituted or unsubstituted aliphatic of 1-20 carbons, substituted or unsubstituted alicyclic of 5-8 carbons, substituted or unsubstituted phenyl, substituted or unsubstituted araliphatic of 7-9 carbons, polyoxyalkylene of formula (I) or heterocyclic of 5-12 atoms $-C-$, $-O-$ or $-N(R^{24})-$, with the further proviso that there are no more than two non-carbon atoms;

Q is $-C(=O)-$, $-C(=O)-O-$, $-(C(=O))_2-O-$, $-C(=O)-N(R^{25})-$, $-(C(=O))_2-N(R^{25})-$ or a direct bond between the nitrogen and $R^{14}$;

$R^{15}$ and $R^{16}$ are independently substituted or unsubstituted aliphatic of 1-8 carbons, substituted or unsubstituted alicyclic of 5-8 carbons, substituted or unsubstituted aryl of 6-12 carbons, substituted or unsubstituted araliphatic of 7-14 carbons or linked together to form a substituted or unsubstituted cycloalkyl ring of 5-8 carbons or a group of formula $$R^{24}-N \begin{array}{c} CH_3 \quad CH_3 \\ \diagdown \diagup \\ C-CH_2 \\ \diagup \quad \diagdown \\ \diagdown \quad \diagup \\ C-CH_2 \\ \diagup \quad \diagdown \\ CH_3 \quad CH_3 \end{array} C;$$

$R^{17}$ is a substituted or unsubstituted aliphatic diradical of 2-20 carbons, substituted or unsubstituted alicyclic diradical of 6-8 carbons, substituted or unsubstituted aryl diradical of 6-10 carbons or any of the $R^{17}$ diradicals containing 1 or 2 heteroatoms $-O-$, $-S-$ or $-N(R^{26})-$, with the further proviso that the cyclic group Z formed contains 5 atoms in the ring;

$R^{18}$ is a substituted or unsubstituted aliphatic diradical of 2-20 carbons, substituted or unsubstituted alicyclic diradical of 6-8 carbons, substituted or unsubstituted aryl diradical of 6-10 carbons or any of the $R^{18}$ diradicals containing 1 or 2 heteroatoms $-O-$ or $-N(R^{26})-$;

$R^{20}$ is hydrogen, substituted or unsubstituted aliphatic of 1-8 carbons, substituted or unsubstituted alicyclic of 5-8 carbons or substituted or unsubstituted araliphatic of 7-8 carbons, $R^{24}$ is hydrogen, substituted or unsubstituted aliphatic of 1-4 carbons, substituted or unsubstituted araliphatic of 7-10 carbons or substituted or unsubstituted aliphatic acyl of 2-6 carbons or substituted or unsubstituted benzoyl;

$R^{25}$ and $R^{26}$ are independently hydrogen or methyl; and

M is hydrogen or sodium ion.

3. The compound of claim 2 wherein $R^1, R^2, R^3$ and $R^4$ are independently hydrogen, $-O-R^9$ or chloro;

X is $-O-$ or a direct bond between the aromatic nucleus and $R^5$;

$R^5$ is a substituted or unsubstituted aliphatic diradical of 1-3 carbons, substituted or unsubstituted alicyclic diradical of 5-8 carbons, substituted or unsubstituted phenylene or substituted or unsubstituted araliphatic diradical of 7-12 carbons;

$R^7$ is hydrogen, methyl or ethyl;

$R^8$ is substituted or unsubstituted aliphatic of 1-8 carbons or substituted or unsubstituted phenyl;

$R^{11}$ and $R^{12}$ are hydrogen;

$R^{13}$ is hydrogen, substituted or unsubstituted aliphatic of 1-8 carbons, or substituted or unsubstituted phenyl;

$R^{14}$ is hydrogen, substituted or unsubstituted aliphatic of 1-10 carbons, substituted or unsubstituted cyclohexyl, substituted or unsubstituted phenyl or substituted or unsubstituted araliphatic of 7-14 carbons, polyoxyalkylene of general formula (I), and when heterocyclic, $R^{14}$ is substituted 2,2,6,6-tetraalkyl-4-piperidinyl;

Q is $-C(=O)-$, $-C(=O)-O-$, or a direct bond between the nitrogen and $R^{14}$;

$R^{24}$ is hydrogen, methyl, acetyl or benzoyl;

$R^{25}$ is hydrogen; and

M is hydrogen.

4. The compound of claim 3 wherein $R^{17}$ and $R^{18}$ are independently tetrabromo-o-phenylene, toluene-2, alpha-diyl, oxybismethylene, thiobismethylene, 1,8-naphthylenediyl, hexachloronorbornene-1,2-diyl, o-phenylene, 1,2-ethenediyl, 4-methylcyclohexane-1,2-diyl or eicosane-1,2-diyl.

5. The compound of claim 3 wherein $R^{15}$ and $R^{16}$ are independently alkyl of 1-6 carbons or substituted or unsubstituted phenyl or $R^{15}$ and $R^{16}$ are linked to form a substituted or unsubstituted cyclohexane ring or a 2,2,6,6-tetramethylpiperidine ring.

6. The compound 2-(4-benzoyl-3-hydroxyphenoxy)acetyl hydrazide according to claim 1.

7. The compound 2-(2-hydroxybenzoyl)benzoic acid hydrazide according to claim 1.

8. The compound 5-benzoyl-4-hydroxy-2-methoxybenzenesulfonyl hydrazide according to claim 1.

9. The compound N-[2-(4-benzoyl-3-hydroxyphenoxy)acetyl]-N'-benzoylhydrazine according to claim 1.

10. The compound 2-(4-benzoyl-3-hydroxyphenoxy)-N'-phenylacetyl hydrazide according to claim 1.

11. The compound (4-benzoyl-3-hydroxyphenoxy)-N'-(methacryloyl)acetyl hydrazide according to claim 1.

12. The compound ethyl N'-[(4-benzoyl-3-hydroxyphenoxy) and acetyl]hydrazinecarboxylate according to claim 1.

13. The compound N-(4-hydroxy-3,5-di-t-butylbenzoyl)-2-(4-benzoyl-3-hydroxyphenoxy)acetyl hydrazide according to claim 1.

14. The compound 2-hydroxybenzophenone-4,4'-diyloxybis(acetyl hydrazide) according to claim 1.

15. The compound 2-(4-benzoyl-3hydroxyphenoxy)ethyl carbazate according to claim 1.

16. The compound octylphenoxypoly-(ethoxy)ethyl-N'-[(4-benzoyl-3-hydroxyphenoxy)acetyl]hydrazinecarboxylate according to claim 1.

17. The compound 2-(4-benzoyl-3-hydroxyphenoxy)ethyl-N'-[(4-benzoyl-3-hydroxyphenoxy)acetyl]hydrazinecarboxylate according to claim 1.

* * * * *